United States Patent
Bonde

(10) Patent No.: US 9,789,236 B2
(45) Date of Patent: Oct. 17, 2017

(54) IMPLANTABLE HEART PUMP CONTROLLER

(71) Applicant: Yale University, New Haven, CT (US)

(72) Inventor: Pramod Bonde, Woodbridge, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 14/858,746

(22) Filed: Sep. 18, 2015

(65) Prior Publication Data

US 2016/0151553 A1    Jun. 2, 2016

Related U.S. Application Data

(63) Continuation-in-part of application No. 14/213,256, filed on Mar. 14, 2014.

(Continued)

(51) Int. Cl.
  *A61M 1/12* (2006.01)
  *A61M 1/10* (2006.01)
  *H04W 12/06* (2009.01)

(52) U.S. Cl.
  CPC .......... *A61M 1/1086* (2013.01); *A61M 1/101* (2013.01); *A61M 1/12* (2013.01); *A61M 1/122* (2014.02); *H04W 12/06* (2013.01); *A61M 2205/3507* (2013.01); *A61M 2205/3523* (2013.01); *A61M 2205/52* (2013.01); *A61M 2205/8206* (2013.01); *A61M 2205/8243* (2013.01); *A61M 2230/06* (2013.01)

(58) Field of Classification Search
  CPC .... A61M 1/1086; A61M 1/128; A61M 1/101; A61M 2205/3507; H04W 12/16
  See application file for complete search history.

(56) References Cited

U.S. PATENT DOCUMENTS 4,809,681 A    3/1989    Kantrowitz et al.
6,669,624 B2    12/2003    Frazier
(Continued)

FOREIGN PATENT DOCUMENTS

WO    2011146661    11/2011

OTHER PUBLICATIONS

Sample, A.P., et al. (2011) "Analysis, experimental results, and range adaptation of magnetically coupled resonators for wireless power transfer," IEEE Transactions on Industrial Electronics, 58(2):544-554.

(Continued)

*Primary Examiner* — Paula J Stice
(74) *Attorney, Agent, or Firm* — Riverside Law LLP

(57) ABSTRACT

The present invention provides devices, systems, and methods for control of and communication with ventricular assist devices. In certain embodiments, the invention includes an implantable controller that is operatively programmed to direct physiological flow through a ventricular assist device that can be substantially synchronized to the cardiac cycle of the subject. In certain embodiments, the implantable controller is also communicatively connected to an external control unit, such that the implantable controller can transmit data to the external control unit, and instructions can be sent from the external control unit to the implantable controller. In certain embodiments, a system and method for secure communication between a remote device and the implanted ventricular assist device is provided.

20 Claims, 19 Drawing Sheets

Related U.S. Application Data

(60) Provisional application No. 61/782,663, filed on Mar. 14, 2013.

(56) References Cited

U.S. PATENT DOCUMENTS

| | | |
|---|---|---|
| 6,764,373 B1 | 7/2004 | Osawa et al. |
| 7,986,122 B2 | 7/2011 | Fornage et al. |
| 8,076,801 B2 | 12/2011 | Karalis et al. |
| 8,143,746 B2 | 3/2012 | Marzetta et al. |
| 8,299,652 B2 | 10/2012 | Sample et al. |
| 8,446,045 B2 | 5/2013 | Smith et al. |
| 8,618,766 B2 | 12/2013 | Anderson et al. |
| 8,767,871 B2 | 7/2014 | Park et al. |
| 8,864,644 B2 | 10/2014 | Yomtov |
| 2004/0172077 A1 | 9/2004 | Chinchoy et al. |
| 2008/0183287 A1 | 7/2008 | Ayre |
| 2010/0030304 A1 | 2/2010 | Haubrich et al. |
| 2010/0052811 A1 | 3/2010 | Smith et al. |
| 2010/0187913 A1 | 7/2010 | Smith et al. |
| 2011/0156493 A1 | 6/2011 | Bennett |
| 2011/0304408 A1 | 12/2011 | McKinzie, III |
| 2012/0007690 A1 | 1/2012 | Van Bezooijen |
| 2012/0080957 A1 | 4/2012 | Cooper et al. |
| 2012/0153738 A1 | 6/2012 | Karalis et al. |
| 2012/0235636 A1 | 9/2012 | Partovi |
| 2012/0243579 A1 | 9/2012 | Premakanthan et al. |
| 2012/0248888 A1 | 10/2012 | Kesler et al. |
| 2013/0310630 A1 | 11/2013 | Smith et al. |
| 2014/0015328 A1 | 1/2014 | Beaver et al. |
| 2014/0070623 A1 | 3/2014 | Hall et al. |

OTHER PUBLICATIONS

Waters, B.H., et al. (2012) "Powering a Ventricular Assist Device (VAD) With the Free-Range Resonant Electrical Energy Delivery (FREE-D) System," Proceedings of the IEEE, 100(1):138-149.

Heidenreich, P.A., et al. (2013) "Forecasting the impact of heart failure in the United States: a policy statement from the American Heart Association," Crit Heart Fail, 6(3):606-19.

Roger, V.L., et al. (2012) "Heart disease and stroke statistics—2012 update: a report from the American Heart Association," Circulation, 125(1):e2-220.

Stehlik, J., et al. (2010) "The Registry of the International Society for Heart and Lung Transplantation: twenty-seventh official adult heart transplant report—2010," J Heart Lung Transplant, 29(10):1089-1103.

Sivaratnam, K. and Duggan, J.M. (2002) "Left ventricular assist device infections: three case reports and a review of the literature," ASAIO J, 48(1):2-7.

Simon, D., et al. (2005) "Left ventricular assist device-related infection: treatment and outcome," Clin Infect Dis, 40(8):1108-1115.

Slaughter, M.S., et al. (2009) "Advanced heart failure treated with continuous-flow left ventricular assist device," N Engl J Med, 361(23):2241-2251.

Pagani, F.D., et al. (2009) "Extended mechanical circulatory support with a continuous-flow rotary left ventricular assist device," J Am Coll Cardiol, 54(4):312-321.

Demirozu, Z.T., et al. (2011) "Arteriovenous malformation and gastrointestinal bleeding in patients with the HeartMate II left ventricular assist device," J Heart Lung Transplant, 30(8):849-853.

Crow, S., et al. (2009) "Gastrointestinal bleeding rates in recipients of nonpulsatile and pulsatile left ventricular assist device," J Thorac Cardiovasc Surg, 137(1):208-215.

Birks, E.J., et al. (2006) "Left ventricular assist device and drug therapy for the reversal of heart failure," N Engl J Med, 355(18):1873-1884.

Li, Y.Y., et al. (2001) "Downregulation of matrix metalloproteinases and reduction in collagen damage in the failing human heart after support with left ventricular assist devices," Circulation, 104(10):1147-1152.

Amir, O., et al. (2006) "Peripheral vascular reactivity in patients with pulsatile vs axial flow left ventricular assist device support," J Heart Lung Transplant, 25(4):391-394.

Westaby, S., et al. (2007) "Circulatory support with attenuated pulse pressure alters human aortic wall morphology," J Thorac Cardiovasc Surg, 133(2):575-576.

Pirbodaghi, T., et al. (2013) "Asymmetric speed modulation of a rotary blood pump affects ventricular unloading," Eur J Cardiothorac Surg, 43(2):383-388.

Cowger, J., et al. (2010) "The development of aortic insufficiency in left ventricular assist device-supported patients," Cire Heart Fail, 3(6):668-674.

Bishopric, N.H. (2005) "Evolution of the heart from bacteria to man," Ann N.Y. Acad Sci, 1047:13-29.

Akimoto, T., et al. (1999) "Rotary blood pump flow spontaneously increases during exercise under constant pump speed: results of a chronic study," Artif Organs, 23(8):797-801.

Parnis, S.M., et al. (1997) "Progress in the development of a transcutaneously powered axial flow blood pump ventricular assist system," ASAIO J, 43(5):M576-M580.

Waters, T., et al. (1999) "Motor feedback physiological control for a continuous flow ventricular assist device," Artif Organs, 23(6):480-486.

Choi, S., et al. (2001) "A Sensorless Approach to Control of a Turbodynamic Left Ventricular Assist System," IEEE Trans on Control Systems Technol, 9(3):473-482.

Boston, J., et al. (2000) "Control issues in rotary heart assist devices," Proc American Control Conf, pp. 3473-3477.

Yoshizawa, M., et al. (2002) "Sensorless estimation of pressure head and flow of a continuous flow artificial heart based on input power and rotational speed," ASAIO J, 48(4):443-448.

Ayre, P.J., et al. (2000) "Sensorless flow and head estimation in the VentrAssist rotary blood pump," Artif Organs, 24(8):585-588.

Tsukiya, T., et al. (1997) "Use of motor current in flow rate measurement for the magnetically suspended centrifugal blood pump," Artif Organs, 21(5):396-401.

Karantonis, D.M., et al. (2007) "Noninvasive pulsatile flow estimation for an implantable rotary blood pump," Conf Proc IEEE Eng Med Biol Soc, 2007:1018-1021.

Giridharan, G.A. and Skliar, M. (2006) "Physiological control of blood pumps using intrinsic pump parameters: a computer simulation study," Artif Organs, 30(4):301-307.

Deng, M.C., et al. (2003) "Mechanical Circulatory Support device database of the International Society for Heart and Lung Transplantation: first annual report—2003," J Heart Lung Transplant, 22(6):653-662.

Holman, W.L., et al. (2009) "Predictors of death and transplant in patients with a mechanical circulatory support device: a multi-institutional study," J Heart Lung Transplant, 28(1):44-50.

Miller, L.W., et al. (2007) "Use of a continuous-flow device in patients awaiting heart transplantation," N Engl J Med, 357(9):885-896.

Holman, W.L., et al. (2004) "Infection in permanent circulatory support: experience from the REMATCH tria," J Heart Lung Transplant, 23(12):1359-1365.

Martin, S.I., et al. (2010) "Effect of body mass index and device type on infection in left ventricular assist device support beyond 30 days," Interact Cardiovasc Thorac Surg, 11(1):20-23.

Holman, S.L., et al. (2010) "Device related infections: are we making progress?" J Card Surg, 25(4):478-483.

Raymond, A.L., et al. (2010) "Obesity and left ventricular assist device driveline exit site infection," ASAIO J, 56(1):57-60.

Zierer, A., et al. (2007) "Late-onset driveline infections: the Achilles' heel of prolonged left ventricular assist device support," Ann Thorac Surg, 84(2):515-520.

Baddour, L.M., et al. (2003) "Nonvalvular cardiovascular device-related infections," Circulation, 108(16):2015-2031.

Schaffer, J.M., et al. (2010) "Infectious complications after pulsatile-flow and continuous-flow left ventricular assist device implementation," J Heart Lung Transplant, 30(2):164-174.

Siegenthaler, M.P., et al. (2003) "The Jarvik 2000 is associated with less infections than the HeartMate left ventricular assist device," Eur J Cardiothroac Surg, 23(5):748-754, discussion 754-755.

(56) References Cited

OTHER PUBLICATIONS

Ford, O. (Feb. 1, 2011) "Analysts see HeartWare taking lead in LVAD market position," Medical Device Daily, http://www.medicaldevicedaily.com/servlet/com.accumedia.web.Dispatcher?next—MDD_Alert02012011b.

Moskowitz, A.J., et al. (2001) "The cost of long-term LVAD implantation," Ann Thorac Surg, 71(3 Suppl):S195-S198, discussion S203-S204.

Oz, M.C., et al. (2003) "Left ventricular assist devices as permanent heart failure therapy: the price of progress," Ann Surg, 238(4):577-583, discussion 583-585.

wikipedia.com (accessed online Jan. 22, 2015) "Ventricular assist device," http://en.wikipedia.org/wiki/Ventricular_assist_device.

Slaughter, M., et al. (2010) "Transcutaneous energy transmission for mechanical circulatory support systems: history, current status, and future prospects," J Cardiac Surg, 25(4):484-489.

Philipose, M., et al. (2005) "Battery-free wireless identification and sensing," IEEE Pervasive Computing, 4(1):37-45.

Kurs, A., et al. (2007) "Wireless power transfer via strongly coupled magnetic resonances," Science, 317(5834):83-86.

Sample, A.P., et al. (2013) "Enabling Seamless Wireless Power Delivery in Dynamic Environments," Proceedings of the IEEE, 101(6):1343-1358.

Christ, A., et al. (2013) "Evaluation of Wireless Resonant Power Transfer Systems with Human Electromagnetic Exposure Limits," IEEE Trans on Electromagnetic Compatibility, 55(2):265-274.

Schocken, D.D., et al. (2008) "Prevention of Heart Failure," Circulation, 117:2544-2565.

The Economist Online (Apr. 12, 2011) "A Wireless Heart," http://www.economist.com/blogs/babbage/2011/04/technology_monitor_0.

Thoratec Corporation (Jan. 11, 2011) "Thoratec Corporation Annual Report 2010," http://media.corporate-ir.net/media_files/irol/95/95989/2010AR/_pdf/Thoratec-2010Form10K.pdf.

The Guardian (Jul. 20, 2009) "Nissan's plug-free electric car," http://www.guardian.co.uk/business/2009/jul/20/nissan-electric-car-plug-free.

Weingartner, M. (Jul. 8, 2010) "Wireless Power—Wireless Resonant Energy Link (WREL)," http://newsroom.intel.com/docs/DOC-1119.

Waters, B.H., et al. (2014) "Innovative Free-Range Resonant Electrical Energy Delivery System (FREE-D System) for a Ventricular Assist Device Using Wireless Power," ASAIO J, 60(1):31-37.

Waters, B.H., et al. (2012) "Adaptive Impedance Matching for Magnetically Coupled Resonators," PIERS Proceedings, Moscow, Russia, pp. 694-701.

Sample, A., and Smith, J. (2009) "Experimental results with two wireless power transfer systems," IEEE Radio and Wireless Symposium, pp. 16-18.

Brown, W. (1984) "The history of power transmission by radio waves," IEEE Trans on Microwave Theory and Techniques, 32(9):1230-1242.

McSpadden, J., and Manikins, J. (202) "Space solar power programs and microwave wireless power transmission technology," IEEE Microwave Magazine, 3(4):46-57.

Cannon, B., et al. (2009) "Magnetic resonant coupling as a potential means for wireless power transfer to multiple small receivers," IEEE Trans on Power Electronics, 24(7):1819-1825.

Low, Z.N., et al. (2009) "Design and test of a high-power high-efficiency loosely coupled planar wireless power transfer system," IEEE Trans on Industrial Electronics, 56(5):1801-1812.

Casanova, J., et al. (2009) "A loosely coupled planar wireless power system for multiple receivers," IEEE Trans on Industrial Electronics, 56(8):3060-3068.

Imura, T. (2010) "Study on maximum air-gap and efficiency of Magnetic Resonant Coupling for Wireless Power Transfer using Equivalent Circuit," 2010 IEEE International Symposium on Industrial Electronics, pp. 3664-3669.

Christ, A., et al. (2011) "Numerical electromagnetic analysis of human exposure for wireless power transfer systems," Proc of 10th International Congress of Eur Bioelectromagnetics Assoc, 2 pages.

Thompson, M., and Fidler, J. (2004) "Determination of the impedance matching domain of impedance matching networks," IEEE Trans on Circuits and Systems I: Regular Papers, 51(10):2098-2106.

Sun, Y., and Fidler, J. (1996) "Design method for impedance matching networks," IEEE Proc on Circuits, Devices and Systems, 143(4):186-194.

Gordon, R.J., et al. (2006) "Ventricular assist device-related infections," Lancet Infect Dis, 6(7):426-437.

Allen, J.G., eta l. (2010) "Quality of life and functional status in patients surviving 12 months after left ventricular assist device implantation," J Heart Lung Transplant, 29(3):278-285.

Wilson, W., et al. (2008) "Prevention of infective endocarditis," J Amer Dent Assoc, 139(Supp 1):S3-S24.

Monkowski, D.H., et al. (2007) "Infections associated with ventricular assist devices: Epidemiology and effect on prognosis after transplantation," Transpl Infecct Dis, 9(2):114-120.

Topkara, V.K., et al. (2010) "Infectious complications in patients with left ventricular assist device: Etiology and outcomes in the continuous-flow era," Ann Throac Surg, 90(4):1270-1277.

Mizannojehdehi, A., et al. (2006) "Design and analysis of a class-e frequency-controlled transcutaneous energy transfer system," Proc IEEE Eelctron Circuits Systm Conf, pp. 21-24.

Haj-Yahia, S., et al. (2007) "Midterm experience with the Jarvik 2000 axial flow left ventricular assist device," J Thorac Cardiovasc Surg, 134(1):199-203.

El-Banayosy, A., et al. (2003) "Preliminary experience with the LionHeart left ventricular assist device in patients with end-stage heart failure," Ann Thorac Surg, 75(5): 1469-1475.

Ozeki, T., et al. (2003) "Functions for detecting malposition of transcutaneous energy transmission coils," ASAIO J, 49:469-474.

Smith, J., et al. (2011) "Innovative Free-Range Resonant Electrical Energy Delivery System (FREE-D System) for a Ventricular Assist Device Using Wireless Power," Proc. ASAIO 31st Annu Conf, Washington, DC, Jun. 10-12, 2011, p. 102.

Frickey, D.A. (1994) "Conversions Between S, Z, Y, h, ABCD, and T Parameters which are Valid for Complex Source and Load Impedances," IEEE Trans Microwave Theory and Techniques, 42(2):205-211.

Raval, P., et al. (2011) "A wireless power transfer system for lower power electronics charging applications," 6th Conf on Industrial Electronics and Applications, pp. 520-525.

Huang, G.T. (Sep. 29, 2009) "Intel Labs Seattle Shows Off New Sensing Interfaces, Self-Charging Robot, Wireless Power," http://www.xconomy.com/seattle/2009/09/29/intel-labs-seattle-shows-off-new-sensing-interfaces-self-charging-robot-wireless-power/.

bccresearch.com (Feb. 2013) "Robotics: Technologies and Global Markets," http://www.bccresearch.com/market-research/engineering/robotics-market-technologies-eng001d.html.

Hollister, S. (Apr. 17, 2013) "From Touchstone to flashpoint: the wireless charging standards war," http://www.theverge.com/2013/4/17/4236980/wireless-charging.

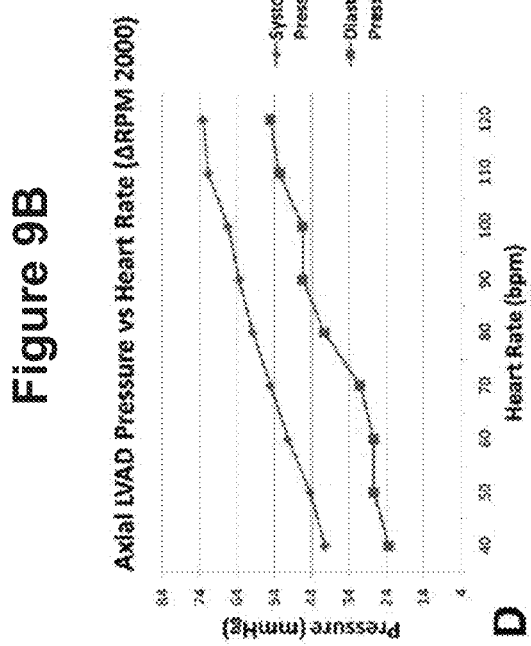
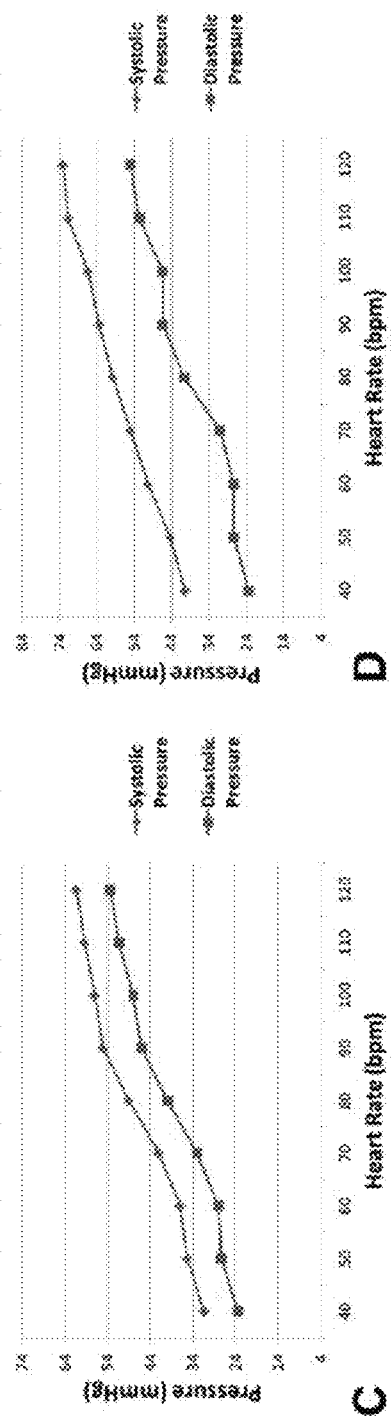
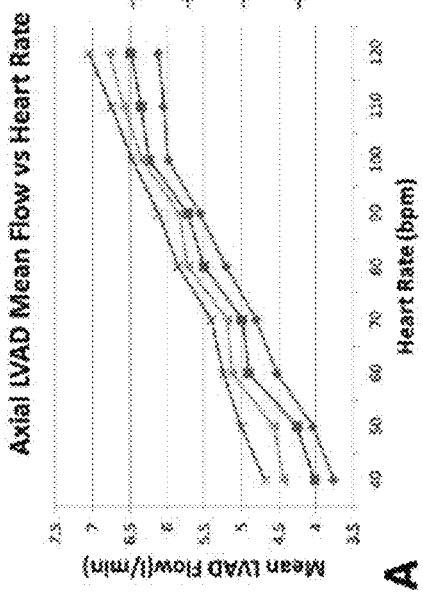
Figure 9A
Figure 9B
Figure 9C
Figure 9D

```
high = r;
if(high-low > 500){
    double bpm = 60000.00 / timeElapsed * 4 ;
    double bpm1 = pow(bpm, 0.976573);
    double bpm2 = bpm1*1.060415;
    if(BLE_Firmata.good){
        //BLE_Firmata.sendAnalog(10 , bpm2);
        //Serial.println("bpm is:"+bpm2);
    }
    runDown = (.4/.7)*(60/bpm2)/.0002466666667;
    timeElapsed=0;
    high =0;
    low = 1023;
}
}
```

Figure 16

IMPLANTABLE HEART PUMP CONTROLLER

CROSS-REFERENCE TO RELATED APPLICATIONS

This application is a continuation in part of U.S. Non-Provisional application Ser. No. 14/213,256 filed on Mar. 14, 2014, which claims priority to U.S. Provisional Application No. 61/782,663 filed on Mar. 14, 2013, both of which are incorporated by reference herein in their entireties.

BACKGROUND OF THE INVENTION

By 2030, it is anticipated that 10 million people in the United States will live with heart failure (1/33 people) (Heidenreich et al., 2013, Crit Heart Fail, 6: 606-19; Roger et al., 2012, Circulation, 125: e2-220. However, the available donor hearts remain stagnant at approximately 2000 per year (Stehlik et al., 2010, J Heart Lung Transplant, 39: 1089-103). In recent years, implantable left ventricular assist devices (LVADs) have offered another option to this ill population. Although showing a survival advantage, the earlier pneumatically driven positive displacement pumps showed high mechanical failure due to wear and tear associated with multiple moving parts and associated friction. The technologic improvement of rotary pumps with a single moving part has led to increased durability and patient survival compared with their earlier generations both as a bridge to transplant and as destination therapy. However, the improved durability of rotary blood pumps comes at the compromise of having a pulseless continuous blood flow.

Despite the technologic advances to the pump body, the requirement of a transcutaneous driveline to conduct power (previously needed for shuttling air for pulsatile devices), controller algorithms, and data exchange between the pump and the extracorporeal controller remains unchanged. Despite the benefits of this technology, driveline-associated infections are a common and devastating complication (Sivaratnam and Duggan, 2002, ASAIO J, 48: 2-7; Simon et al., 2005, Clin Infect Dis., 40: 1108-15) that causes a significant negative impact on a patient's quality of life and increased medical cost (Slaughter et al., 2009, N Engl J Med, 361: 2241-51. The presence of nonphysiologic pulseless blood flow in patients with long-term LVAD support has been implicated in increased gastrointestinal bleeding (Pagani et al., 2009, J Am Coll Cardiol, 54: 312-21; Demirozu et al., 2011, J Heart Lung Transplant, 30: 849-53; Crow et al., 2009, J Thorac Cardiovasc Surg, 137: 208-15), limited cardiac unloading (Birks et al., 2006, N Engl J Med, 355: 1873-84; Li et al., 2001, Circulation, 104: 1147-52), vascular malformations (Amir et al., 2006, J Heart Lung Transplant, 25: 391-4; Westaby et al., 2007, J Thorac Cardiovasc Surg, 133: 575-6), and aortic incompetence (Pirbodaghi et al., 2013, Heart Fail Rev; Cowger et al., 2010, 3: 668-74). Moreover, because successful LVAD explantation occurs less often with continuous-flow pumps, concerns have been raised regarding their use in patients with a potential for myocardial recovery. In addition, conventional LVADs introduce the risk of ventricular diastolic collapse, caused by an overwhelming pressure increase from the pump. Because LVADs flow continuously, they are unable to adjust between the systolic and diastolic phases of the cardiac cycle.

Thus, there is a need in the art for heart pump devices, systems and communication interfaces to provide physiological flow that better mimics the natural heart function, and provides patients and physicians with better access to pump controls and better feedback regarding pump performance. The present invention satisfies this unmet need.

SUMMARY OF THE INVENTION

In one embodiment, a system for remote communication with an implantable ventricular assist device includes a ventricular assist device storing a first key-id to authenticate a communication session between the implantable ventricular assist device and a mobile device, and a software platform configured to verify a second key-id to authenticate a communication session between the mobile device and the software platform, the software platform further configured to verify a patient specific key received from a remote device to authenticate a communication session between the software platform and a remote device, where the software platform is configured to establish a communication session to send values from the remote device to the implantable ventricular assist device based on verifying all of the first key-id, the second key-id and the patient specific key. In one embodiment, the patient specific key is based on the first key-id. In one embodiment, the the software platform is configured to generate the second key-id after detecting an initialization of a connection between the mobile device and the software platform. In one embodiment, the software platform is a server. In one embodiment, the remote device is a user computer. In one embodiment, the remote device is configured to accept input of the values through a web-based portal. In one embodiment, the values include at least one of systole power and diastole power. In one embodiment, the values include all of systole power, diastole power and the patient specific key. In one embodiment, the implantable ventricular assist device is configured to send feedback to the remote device after verifying all of the first key-id, the second key-id and the patient specific key. In one embodiment, the feedback includes at least one of a heart rate and a pump speed.

In one embodiment, a method for remote communication with an implantable ventricular assist device includes the steps of verifying a first key-id stored on an implantable ventricular assist device to authenticate a communication session between the implantable ventricular assist device and a mobile device, verifying a second key-id to authenticate a communication session between the mobile device and a software platform, and verifying a patient specific key to authenticate a communication session between the software platform and a remote device, where a communication session to send values from the remote device to the implantable ventricular assist device is authenticated based on verifying all of the first key-id, the second key-id and the patient specific key. In one embodiment, the patient specific key is based on the first key-id. In one embodiment, the second key-id is generated at initialization of connection between the mobile device and the software platform. In one embodiment, the software platform is a server. In one embodiment, the remote device is a user computer. In one embodiment, the method includes the step of accepting input of the values through a web-based portal. In one embodiment, the values include at least one of systole power and diastole power. In one embodiment, the values include all of systole power, diastole power and the patient specific key. In one embodiment, the method includes the step of sending feedback from the implantable ventricular assist device to the remote device after verifying all of the first key-id, the second key-id and the patient specific key. In one embodiment, the feedback includes at least one of a heart rate and a pump speed.

In one embodiment, an implantable ventricular assist device controller includes at least one processing unit, an input device and an output device, where the controller is operatively programmed to direct physiological flow through a ventricular assist device that is substantially synchronizable to a cardiac cycle of the subject in whom the ventricular assist device is implantable, and where the controller is operatively programmed to revert from a pulsatile pumping mode to a continuous flow mode when a connection error is detected. In one embodiment, the controller is configured to receive input for controlling physiological flow from a wireless connection with an external device. In one embodiment, the device includes at least one electrode for receiving an EKG signal from the subject. In one embodiment, the device includes a receiver resonator for wireless energy transfer.

In one embodiment, a method of controlling a ventricular assist device implanted in a subject includes the steps of operatively connecting an implantable controller to a ventricular assist device implanted in a subject, synchronizing physiological flow through the ventricular assist device to a cardiac cycle of the subject via the controller, and reverting from a pulsatile pumping mode to a continuous flow mode when a connection error is detected. In one embodiment, the method includes changing the speed of the ventricular assist device based on at least one physiological signal measured in the subject. In one embodiment, the method includes receiving input for controlling physiological flow from a wireless connection with an external device.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 5B depicts an external graphical user interface embedded in a smartphone. This platform displays and controls an LVAD pump by wireless communication or Internet access.

FIG. 6A is a graph depicting pump speed versus power consumption for the controller of the invention compared to a conventional controller. FIG. 6B is a graph depicting flow versus power consumption for the controller of the invention compared to a conventional controller.

FIG. 7A shows a higher pump speed during diastole and a lower speed during systole for the pulsatile mode 1. This technique reduces the preload of the heart and therefore can be used for myocardial recovery. FIG. 7B shows a higher pump speed during systole and a lower speed during diastole for the pulsatile mode 2. This method can be used to create a larger pulse pressure when it is required.

FIGS. 9A through 9H depict the results of in vitro testing with the HeartMate II (Thoratec Co, Pleasanton, Calif.) pump. Most of these equations are related to a specific MCL. FIG. 9A: The controller adapts to changes in heart rate to create the corresponding mean LVAD flow. The degree of pulsatility also changes the mean flow. The linear regression for this model is as follows: Mean LVAD Flow (L/min)= 0.031333·Heart Rate (beats/min)+0.00024089·ΔRPM (rpms)+2.38056. FIG. 9B: A 10% increase in fraction of systole increases the mean flow in our system by 0.29 L/min; therefore, more flexibility is added to adapt to the patient's everyday life. This relationship is modeled as follows: Mean LVAD Flow (L/min)=0.02486·Heart Rate (beats/min)+ 0.02934·Fraction of Systole (%)+1.8883. FIG. 9C-FIG. 9F: The UMC-Physio changes the systolic and diastolic pressures by increases or decreases in the heart rate. The following equations represent the estimated systolic and diastolic pressures: Systolic Pressure (mm Hg)=0.44014·Heart Rate (beats/min)+0.01041·ΔRPM (rpms)+2.02963 Diastolic Pressure (mm Hg)=0.41806·Heart Rate (beats/min)+0.00042593·ΔRPM (rpms)+4.85185. FIG. 9G: Increments in ΔRPM generate more pulsatility. FIG. 9H: For 2 watts of power, the UMC-Physio produces 5.5 L/min of flow, whereas the HeartMate II controller can create only 3.8 L/min; therefore, our controller is on average more efficient by 17.54%. This result is good evidence for how pump controller optimization and precise control can contribute to the efficiency of an LVAD. The efficiency is estimated by the following: Efficiency (%)=0.08309·Flow$^3$+ 1.897·Flow$^2$+13.907·Flow (L/min)−15.6778. bmp, Beats/min; LVAD, left ventricular assist device; ΔRPM, difference between systolic and diastolic pump speeds; UMC-Physio, ultra-compact implantable physiologic controller.

FIG. 10A: The UMC-Physio increases the mean flow of the centrifugal pump by 0.22 L/min with 10 beats/min in the heart rate. The linear regression model for this graph is Mean LVAD Flow (L/min)=0.0226·Heart Rate (beats/min)+0.000638222·ΔRPM (rpms)+3.7245. FIG. 10B: Confirms that 10% increase in fraction of systole linearly increases the mean LVAD flow by 0.2 L/min. This formula explains this linear regression: Mean LVAD Flow (L/min)= 0.0046·Heart Rate (beats/min)+0.0205·Fraction of Systole (%)+4.09312. FIG. 10C-FIG. 10F: Heart rates up to 80 beats/min will increase the systolic and diastolic pressures produced by our controller. The systolic and diastolic pressures can be estimated by the following formulas: Systolic Pressure (mm Hg)=0.50067·Heart Rate (beats/min)+ 0.02364·ΔRPM (rpms)+31.9855 Diastolic Pressure (mm Hg)=0.26817·Heart Rate (beats/min)+0.00188·ΔRPM (rpms)+32.085. FIG. 10G: Pulse pressure can be easily controlled by the system; the linear regression is modeled as Pulse Pressure (mm Hg)=0.2325·Heart Rate (beats/min)+ 0.02176·ΔRPM (rpms)−0.14. FIG. 10H: Proves that the controller is also more efficient than the HeartWare Ventricular Assist Device controller. The descriptive statistics indicate that our controller is more efficient by a mean of 35.49%. Efficiency is modeled as follows: Efficiency (%)=2.648·Flow$^2$−32.630·Flow (L/min)+132.964. bmp, Beats/min; LVAD, left ventricular assist device; ΔRPM, difference between systolic and diastolic pump speeds; UMC-Physio, ultra-compact implantable physiologic controller.

FIG. 16 is an example of code used to detect an R-wave according to one embodiment.

DETAILED DESCRIPTION

Definitions

Figure 1:
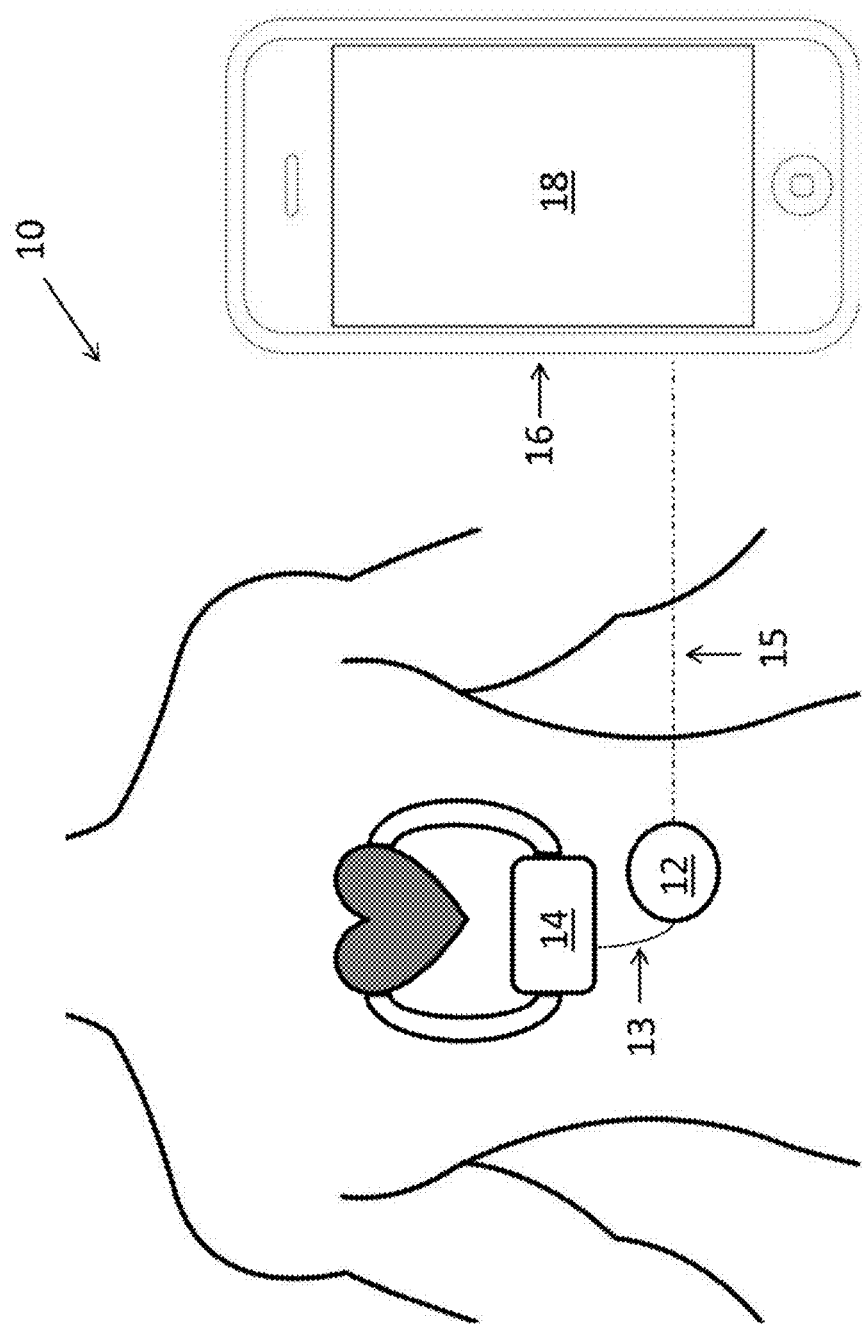
FIG. 1 is a diagram of an exemplary system according to an aspect of the present invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The present invention provides devices, systems and methods for driving physiological flow using a heart pump. For example, in one embodiment, the present invention includes a device that comprises an implantable controller connected to and controlling a heart pump. In certain embodiments, the device provides physiological flow that is synchronized to the heart beat or cardiac cycle of the user. The device may be configured for use with any type of heart pump, including, but not limited to, axial pumps, centrifugal pumps, ventricular assist devices (VADs), RVADs, LVADs, BiVADs, total artificial hearts, and the like. Commercially available pumps suitable for use with the present invention include, but are not limited to, Novacor, HeartMate XVE, HeartMate II, Heartmate III, Incor, Excor Pediatric, Jarvik 2000, MicroMed DeBakey VAD, VentrAssist, MTIHeartL-VAD, C-Pulse, HVAD, MVAD, DuraHeart, Thoratec PVAD, and IVAD (Thoratec). In certain embodiments, the device of the present invention can replace or augment a controller that is commonly used with a particular pump. The present invention may be used to support and/or control cardiac function in patients with conditions including, but not limited to, congestive heart failure, acute heart failure, right heart failure, left heart failure, and the like. In certain embodiments, the device communicates with the heart pump to alter the function of the heart pump. For example, in one embodiment, the device of the invention communicates with the heart pump to alter the properties of blood flow created by the pump.

In certain embodiments, the present invention comprises an implantable controller. The implantable controller of the invention is sometimes referred to herein as the ultra-compact microcontroller, or UMC-Physio. In one embodiment, the controller is a wireless controller and is sized and shaped to be implanted within the body of the user. As such, it eliminates the need for wires connecting the internal heart pump to an extracorporeal unit. In certain embodiments, the controller is implanted subcutaneously.

The controller is sized and shaped to be a compact unit, thereby allowing for easier implantation. In one embodiment, the controller is the shape of a rectangular prism, having a defined length, width, and depth. It should be appreciated that there is no limitation to the particular dimensions of the controller, provided the controller is implantable and retains all desired functionality as contemplated hereinthroughout. For example, in one embodiment, the length of the controller is about 0.1-5 inches. In another embodiment, the length of the controller is about 0.5-2 inches. In another embodiment, the length of the controller is about 1-1.5 inches. In one embodiment, the width of the controller is about 0.1-5 inches. In another embodiment, the width of the controller is about 0.5-2 inches. In another embodiment, the width of the controller is about 1-1.5 inches. In one embodiment, the depth of the controller is about 0.05-2 inches. In another embodiment, the depth of the controller is about 0.1-1 inches. In another embodiment, the depth of the controller is about 0.2-0.5 inches. In a particular embodiment, the controller is about 1.4 inches long×1.2 inches wide×0.2 inches deep.

In one embodiment, the controller comprises a power source. For example, the controller may comprise a long-lasting battery. In another embodiment, the power source is a rechargeable power source, such as a rechargeable battery. In one embodiment, the power source is wirelessly rechargeable. The controller of the invention is not limited to any particular type of power source, but rather encompasses any type of suitable power source as would be understood by those skilled in the art.

In one embodiment, the system comprises a wireless power system for wirelessly powering the implantable controller. For example, in one embodiment, the system comprises magnetically coupled resonators, comprising a source resonator coil and a receiver resonator coil. In one embodiment, the implantable controller comprises a receiver resonator coil, while the source resonator coil is placed outside the body, in the vicinity of the user. In one embodiment, the source resonator coil is comprised within the external control unit.

In a particular embodiment, the invention may be powered by a wireless power system, such as a system as described in U.S. Pat. No. 8,299,652; U.S. Patent Application Publication No. 2013/0310630; Sample et al., 2011, IEEE Transactions, 58(2): 544-554; and Waters et al., 2012, Proceedings of the IEEE, 100(1): 138-149, the entire disclosures of which is incorporated by reference herein in their entireties. For example, the controller may be powered and charged by energy transfer using magnetically coupled resonators (ETMCR). Magnetically coupled resonators induce power transfer between two components through the matching of the resonance frequency between a source resonator and receiver resonator. For example, a source resonator is a coil induced to resonate at a given frequency. A frequency-matched receiver resonator, within some vicinity of the source, is a coil tuned to resonate at the same frequency as the source. Thus, when the source resonator is induced to resonate at the given frequency, the frequency-matched receiver resonator is also induced to resonate, which results in the transfer of power to a component attached to the receiver resonator. For example, in one embodiment, the controller comprises a receiver resonator, or is otherwise attached to a receive resonator, for wirelessly powering the controller. In one embodiment, the invention comprises a source resonator that is magnetically coupled to the receiver resonator. The source resonator may be placed anywhere in the vicinity of the user-implanted receiver resonator. For example, the source resonator can be worn on the body of the user, or placed in the same room or building of the user. In some embodiments, the wireless system comprises a plurality of receiver resonators, wherein the source receiver transfers power to a first receiver resonator, which transfers power to the next receiver resonator, and so forth. In some embodiments, the system comprises a plurality of receiver resonators, wherein the source receiver can transfer power to each of the plurality of receiver resonators. The frequency at which the source resonator resonates is adaptable, thereby allowing the powering of a plurality of receiver resonators, each of which is tuned to resonate at a specific frequency. In one embodiment, the wireless power system of the invention comprises an impedance matching network that produces high efficiency power transfer from the source resonator to a plurality of receiver resonators at either a wide-band frequency range or a single frequency. In one embodiment, the system comprises an adaptive impedance matching network on both the source and receiver sides of the coupled resonators. The one or more adaptive impedance networks of the system allows for efficient power transfer in a dynamic environment, where the source and receiver resonators are in constant movement. Power transfer between magnetically coupled resonators is dependent on distance and orientation, and thus in some instances, power transfer via traditional magnetically coupled resonators would be inefficient in dynamic environments.

As contemplated herein, the device has the ability to monitor the function of the heart pump and/or the cardiac function of the user. In one embodiment, the controller comprises one or more sensing electrodes to sense one or more biosignals from the user. For example, the device comprises one or more sensing electrodes to receive, filter, amplify and analyze an EKG signal. In one embodiment, the device measures real time function and power consumption of the heart pump. For example, the device can measure the pump speed of the pump (e.g. VAD speed). These measures can then be used to derive many variables of pump function including flow, suction event, pressure head of the pump, and occlusion event. The ability of the present invention to determine these variables is beneficial as it would remove the need for long term sensors to be placed within the body.

In one embodiment, the device comprises a telemetry module, a transceiver or other networking component for communicating with an external control unit. For example, the controller uses the telemetry module to send information regarding pump function and cardiac function to the external control unit. The external control unit can comprise any suitable computing device including desktop or mobile devices, laptops, desktops, tablets, smartphones or other wireless digital/cellular phones, wrist watches, televisions or other thin client devices as would be understood by those skilled in the art. Further, the external control unit comprises software that includes a user interface that allows for the changing of controller settings, which can then be transmitted from the external control unit to the implanted controller using the telemetry module. Communication between the external control unit and the implanted controller can be made via any wireless based technology, including, but not limited to radio signals, near field communication systems, hypersonic signal, infrared systems, cellular signals, GSM, and the like.

The controller of the invention controls the function of a heart pump in order to provide a desired blood flow in the user. For example, the controller comprises a drive unit which communicates with the pump to drive the pump motor, thereby controlling blood flow. Accordingly, the implanted controller communicatively connected to the heart pump, such that it sends instructional signals to the heart pump to direct the functionality of the pump. In some embodiments, the controller wirelessly communicates with the heart pump. In other embodiments, the controller is connected to the heart pump via direct wirelines. In other embodiments, the controller is integrated into the housing of the heart pump and is therefore directly connected into the circuitry of the heart pump. In one embodiment, the controller has two modes, continuous flow and pulsatile flow. In the continuous flow mode, the pump speed is adjustable using the user interface of the external control unit by the user or clinician. In the pulsatile flow mode, the pump speed is specifically attuned for the systole and diastole periods of the cardiac cycle of the user. For example, the pump speed is specifically adjusted during systole and diastole such that blood flow is varied during the cardiac cycle. The controller can provide either co-pulsation or counter-pulsation. In co-pulsation, the speed of the pump is increased in systole. In counter-pulse the speed of the pump is increased in diastole. For example, in situations when a better pulse pressure or lower afterload (cardiac recovery) is needed, the pump speed during systole is adjusted to have a higher or lower speed than diastole, respectively. In certain embodiments, pulsatile-flow, as mediated by the controller of the invention, better mimics the heartbeat of the user. This allows for improved physiological function that in certain patients would be preferred to continuous flow regimes.

The determination of systole and diastole, and the control of pump speed during the respective periods can be made in a variety of ways. In one embodiment, the pulsatile flow directed by the controller is synchronized to the measured EKG signals of the user. As used herein, the "pulse" refers to an increase in pump speed of a specified duration. For example, the duration of each pulse is determined based on the detected heart rate. In one embodiment, detection of a particular EKG feature (QRS complex, P-wave, T-wave, etc) serves as a trigger for the beginning and/or end of a pulse. In this way, the pulse dictated by the controller of the invention can be varied in real time, depending on the informational feedback loop of the changing heart rate of the user. In another embodiment, the pulsatile flow is determined by a simulated, desired, target, or commanded EKG signal. For example, the controller may use historical data or averaged data to simulate the EKG signal, which is then used to determine and direct the desired pulse parameters (e.g. timing, duration, etc.). In another embodiment, the pulsatile flow is asynchronous. For example, the heart rate and duration of systole can be manually set using the user interface of the external control unit. These imputed parameters, as well as the choice of co-pulsation or counter-pulsation, then are used by the controller to determine and direct the pulse parameters of the heart pump.

The user interface of the external control unit includes settings that control the specific mode of operation of the controller. For example, the user interface is used to select the type of flow, such as continuous or pulsatile. Further, the user interface is used to determine how the pulsatile flow is determined, EKG synchronized, simulated EKG synchronized, or asynchronous.

In one embodiment, the device of the invention comprises multiple safety features. For example, the device has the ability to detect fault behavior of the controller and/or the pump. Exemplary fault behavior includes exceeding of the maximum commutation frequency and the rotational speed falling below the forced commutation frequency. If a fault behavior is detected by the controller, the motor is turned off and output transistors are turned off. After a designated or programmed time period (e.g. 0-2 seconds), the motor may be restarted. If the abnormality persists, the device may cycle in and out of a protection mode. In case of persistent abnormality, the device comprises a secondary drive unit that resumes the function of the controller. In certain embodiments, the device further comprises overvoltage and/or overcurrent protection circuits. In one embodiment, the device comprises a thermal shutdown (TSD) circuit. The TSD circuit announces an abnormal situation once the die temperature exceeds the rated temperature. After the TSD circuit is disabled, the drive unit of the device resumes its operation. The present invention also provides systems comprising the controller device described herein. For example, as shown in FIG. 1, system 10 includes an implantable controller 12, a heart pump 14, and a computing device functioning as an external control unit 16 that executes a software platform presented on a visual interface 18 of the computing device. Heart pump 14 is in communication with controller 12 via wire 13, and controller 12 is further in wireless communication 15 with external control unit 16. The software platform includes a graphical user interface (GUI) for modulating the function of controller 12 and for displaying information regarding the historical or real-time functionality of heart pump 14, as well as historical or real-time functionality of the subject's cardiac function. In certain embodiments, wireless communication 15 for information transfer to and from implanted controller 10 and external control unit 16 may be via a wide area network and may form part of any suitable networked system understood by those having ordinary skill in the art for communication of data to additional computing devices, such as, for example, an open, wide area network (e.g., the internet), an electronic network, an optical network, a wireless network, a physically secure network or virtual private network, and any combinations thereof. Such an expanded network may also include any intermediate nodes, such as gateways, routers, bridges, internet service provider networks, public-switched telephone networks, proxy servers, firewalls, and the like, such that the network may be suitable for the transmission of information items and other data throughout the system.

As would be understood by those skilled in the art, external control unit 16 may be wirelessly connected to the expanded network through, for example, a wireless modem, wireless router, wireless bridge, and the like. Additionally, the software platform of the system may utilize any conventional operating platform or combination of platforms (Windows, Mac OS, Unix, Linux, Android, etc.) and may utilize any conventional networking and communications software as would be understood by those skilled in the art.

Figure 12:
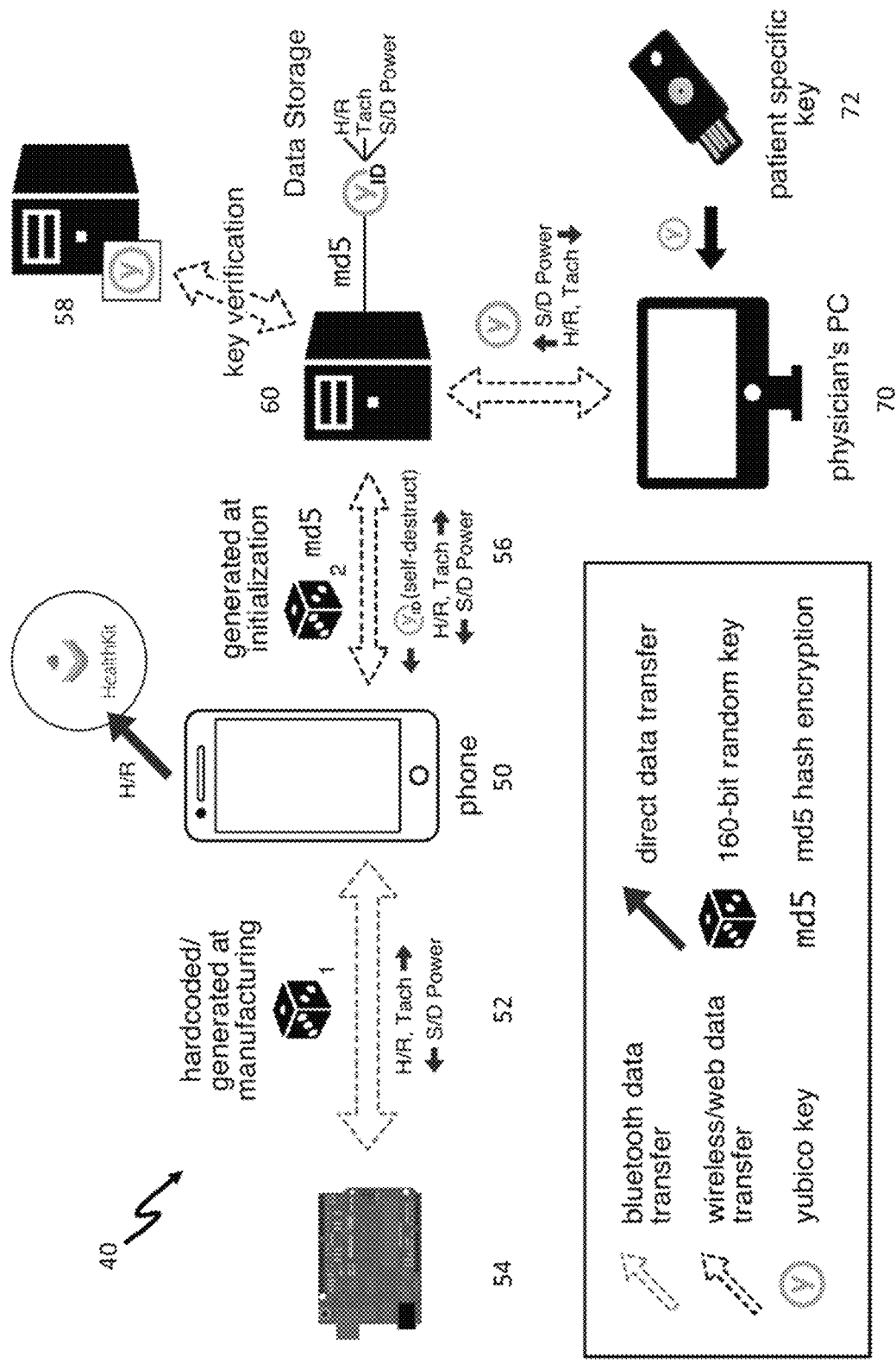
FIG. 12 is a diagram of a security and encryption system according to one embodiment.

To protect data, an encryption standard may be used to protect files from unauthorized interception over the network. Any encryption standard or authentication method as may be understood by those having ordinary skill in the art may be used at any point in the system of the present invention. For example, encryption may be accomplished by encrypting an output file by using a Secure Socket Layer (SSL) with dual key encryption. However, a specific security and encryption protocol can be implemented with the embodiments disclosed herein, according to the exemplary security and encryption system 40 shown in FIG. 12. In one embodiment, a system 40 for remote communication with an implantable ventricular assist device includes a ventricular assist device 54 storing a first key-id to authenticate a communication session between the implantable ventricular assist device 54 and a mobile device 50. A software platform 60 which in certain embodiments is a remote device such as a server, is configured to verify a second key-id to authenticate a communication session between the mobile device 50 and the software platform 60. The software platform 60 is also configured to verify a patient specific key received from a remote device 70 to authenticate a communication session between the software platform 60 and a remote device 70. The software platform 60 is configured to establish a communication session to send values from the remote device 70 to the implantable ventricular assist device 70 based on verifying all of the first key-id, the second key-id and the patient specific key. In one embodiment, the patient's LVAD processor 54 is equipped with a code that is hardcoded or embedded into the processor 54 at manufacturing. The patient's mobile device 50 is equipped with the code during patient setup by an authorized system administrator. The patient's LVAD processor 54 communicates with the patient's mobile device 50 through wireless connection 52 such as Bluetooth, and the connection is setup only after the proper codes are verified. In certain embodiments, the codes have to match. In certain embodiments, one or more of the codes have to match a key, such as a decryption key. In certain embodiments, the code 52 is a randomized code that is generated during a manufacturing process, and hardcoded into the phone at manufacturing. In one embodiment, patient data is sent via a key-verified wireless connection to the patient's mobile device. In one embodiment, the key-verified wireless connection is sent by a key-verified connection to the patient's smart phone. The mobile device, at setup, is given the patient specific key-id in order to write data to the server. In one embodiment, the patient specific key-id is a 160-bit random key, or a Yubico key-id. In one embodiment, the server encrypts values of the patient's Yubico key to verify the phone-server connection. The patient's data is stored in a 'secret' encrypted directory which can only be accessed through a verified patient-specific Yubico key connection, or the encrypted random key specific to the patient's phone. In certain embodiments, the only method of writing values to the device would be through a patient-specific Yubico key, the encrypted random key connection from server to phone, and another encrypted random key Bluetooth connection from phone to LVAD device. In one embodiment, the patient specific key is based on the first key-id. In one embodiment, the software platform 60 is configured to generate the second key-id after detecting an initialization of a connection between the mobile device 50 and the software platform 60. In one embodiment, the software platform 60 is a server. In one embodiment, the remote device 70 is a user computer. In one embodiment, the remote device 70 is configured to accept input of the values through a web-based portal. In one embodiment, the values include at least one of systole power and diastole power. In one embodiment, the values include all of systole power, diastole power and the patient specific key. In one embodiment, the implantable ventricular assist device 54 is configured to send feedback to the remote device 70 after verifying all of the first key-id, the second key-id and the patient specific key. In one embodiment, the feedback includes at least one of a heart rate and a pump speed.

Figure 13:
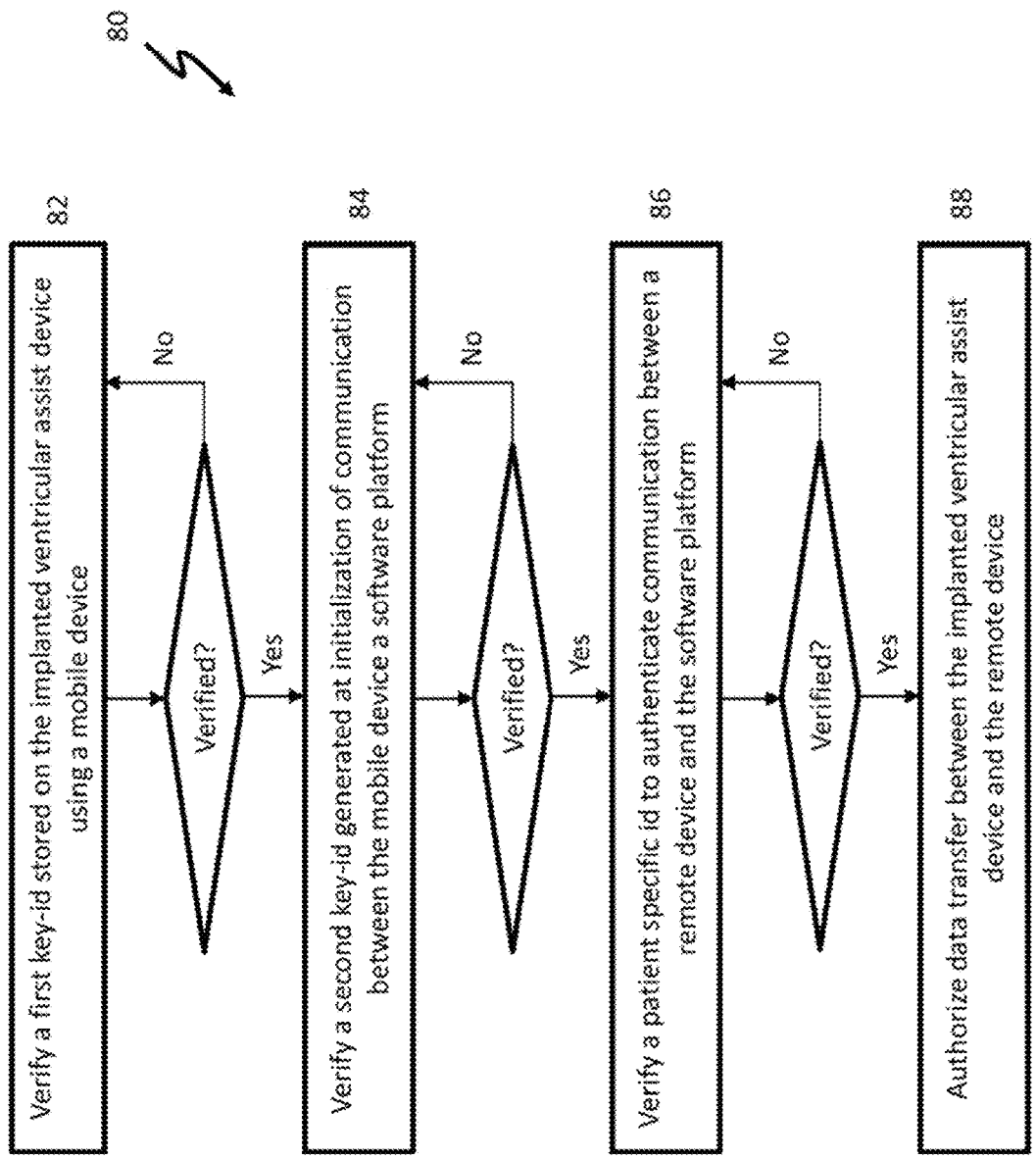
FIG. 13 is a flow chart of a method for authenticating communication sessions according to one embodiment.

A method for remote communication with an implantable ventricular assist device is shown in the flow chart of FIG. 13, according to one embodiment. According to the method 80, a first key-id stored on an implantable ventricular assist device is verified to authenticate a communication session between the implantable ventricular assist device and a mobile device 82. After the first key-id is verified, a second key-id is verified to authenticate a communication session between the mobile device and a software platform 84. After the second key-id is verified, a patient specific key is verified to authenticate a communication session between the software platform and a remote device 86. After final verification, data communications between the remote device (for example, a physician's computer) and the implanted ventricular assist device is authorized to take place 88. In certain embodiments, the verification steps 82, 84 86 take place in a different order. Thus, in one embodiment, a communication session is authenticated to send values such as pump inputs from the remote device to the implantable ventricular assist device based on verifying all of the first key-id, the second key-id and the patient specific key. In one embodiment, the patient specific key is based on the first key-id, or it can even be the same as the first key-id. In one embodiment, the second key-id is generated at initialization of connection between the mobile device and the software platform. In one embodiment, the software platform is a server. In one embodiment, the remote device is a user computer. A web-based portal is used to accept input of the values according to one embodiment. In one embodiment, the values include at least one of systole power and diastole power. The values can also include all of systole power, diastole power and the patient specific key. Feedback can be sent from the implantable ventricular assist device to the remote device only after verifying all of the first key-id, the second key-id and the patient specific key in certain embodiments. The feedback can include at least one of a heart rate and a pump speed. Advantageously, LVAD system according to the embodiments discussed herein utilize wireless, cloud-based storage systems, protected by several layers of encryption, representing a step towards modern, "connected" implants that can securely and efficiently transfer information.

Additionally, the system may limit data manipulation, or information access. Access or use restrictions may be implemented for users at any level. Such restrictions may include, for example, the assignment of user names and passwords that allow the use of the present invention, or the selection of one or more data types that the subservient user is allowed to view or manipulate. In one embodiment, the implanted LVAD communicates wireless with an external mobile device, such as a smart phone (e.g. an iPhone) or a tablet through a wireless communication protocol such as Bluetooth. Software run by the external mobile device allows it to control the LVAD, and monitor the LVAD and other patient parameters measured from sensors such as ECG leads. In one embodiment, the mobile device monitors and controls the device through an internet connection. In one embodiment, an external device, such as a computer station or a second mobile device remotely controls the mobile device which in turn controls the LVAD. The second mobile device remotely controls the mobile device through a wired or a wireless connection, such as an internet connection or cellular communication channels.

Figure 14:
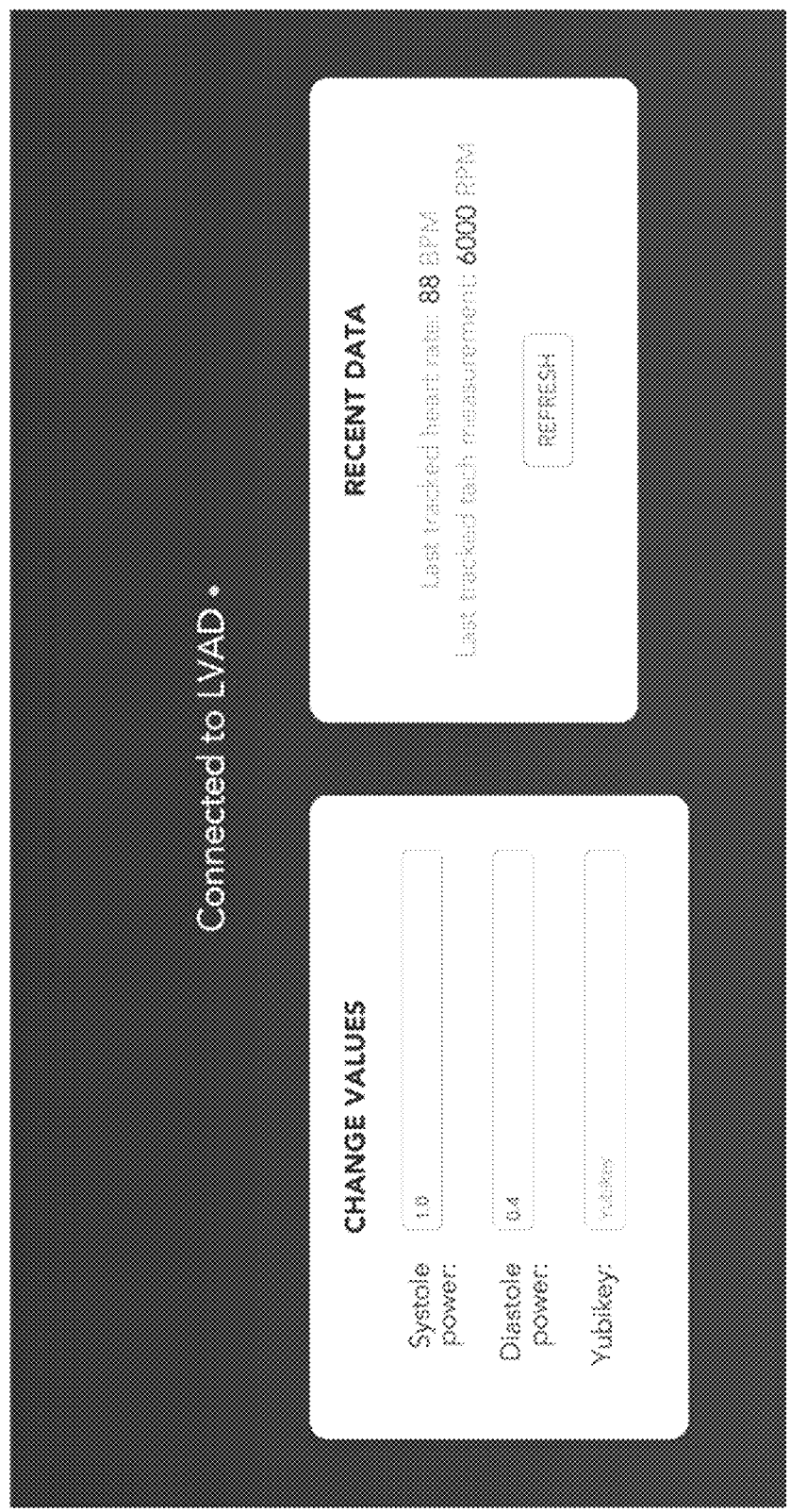
FIG. 14 is a GUI of a web-based portal for physicians to monitor and control implantable devices remotely according to one embodiment.

In one embodiment, a password-protected physician website portal can be used so that a user such as a physician control and monitor the LVAD remotely, as shown in FIG. 14. In one embodiment, the portal verifies to the user that a connection has been established. In one embodiment, an established connection is indicated by a message or a symbol, such as a green light for connected, and a red light for disconnected. In certain embodiments, a yellow light can be indicative of a weak connection. Bars (e.g. 4 bars) can also be used as a graphic to indicate the strength of the connection (e.g. 0 bars for no connection, 1 bar for a weak connection, and up to 4 bars for the strongest connection). Through the portal, the user or physician can view real-time data, such as heart rate, pump speed, and volume flowing through the pump. In one embodiment, the physician can refresh the data to get a real-time measurement. In another embodiment, the displayed data is automatically refreshed. In certain embodiments, automatically refreshed data can reflect a most recent average (e.g. the average over the most recent 5 or 10 cycles of the heart).

In certain embodiments the network provides for telemetric data transfer from the controller to the external control unit, and vice versa. For example, data transfer can be made via any wireless communication 15 may include any wireless based technology, including, but not limited to radio signals, near field communication systems, hypersonic signal, infrared systems, cellular signals, GSM, and the like. In some embodiments, data transfer is conducted without the use of a specific network. Rather, in certain embodiments, data is directly transferred to and from the controller and external control unit via systems described above.

Figure 2B:
FIGS. 2A and 2B are a set of images depicting the graphical user interface of the system on mobile computing devices, including a smartphone (FIG. 2A) and a watch (FIG. 2B).
Figure 2A:
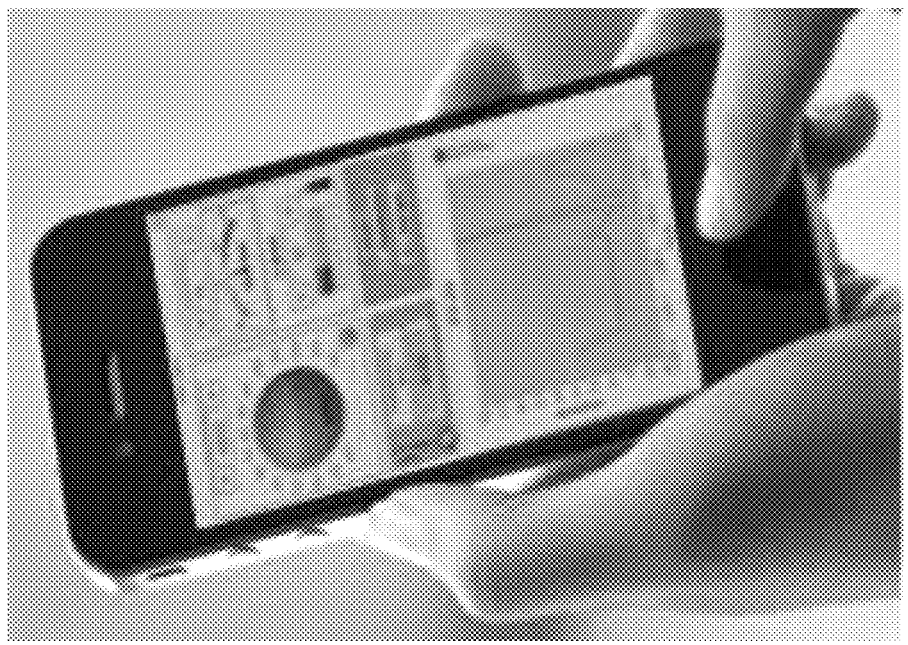

As described elsewhere herein, external control unit 16 may be any computing device including, desktop or mobile devices, laptops, desktops, tablets, smartphones or other wireless digital/cellular phones, wrist watches, televisions or other thin client devices as would be understood by those skilled in the art. In one embodiment, the computing device is a smartphone (FIG. 2A) or it may be a watch (FIG. 2B). The computing devices may include at least one processor, standard input and output devices, as well as all hardware and software typically found on computing devices for storing data and running programs, and for sending and receiving data over a network, if needed. As mentioned previously, external control unit 16 comprises software for displaying controller 12 and pump 14 function and for modulating the function of controller 12.

Figure 3:
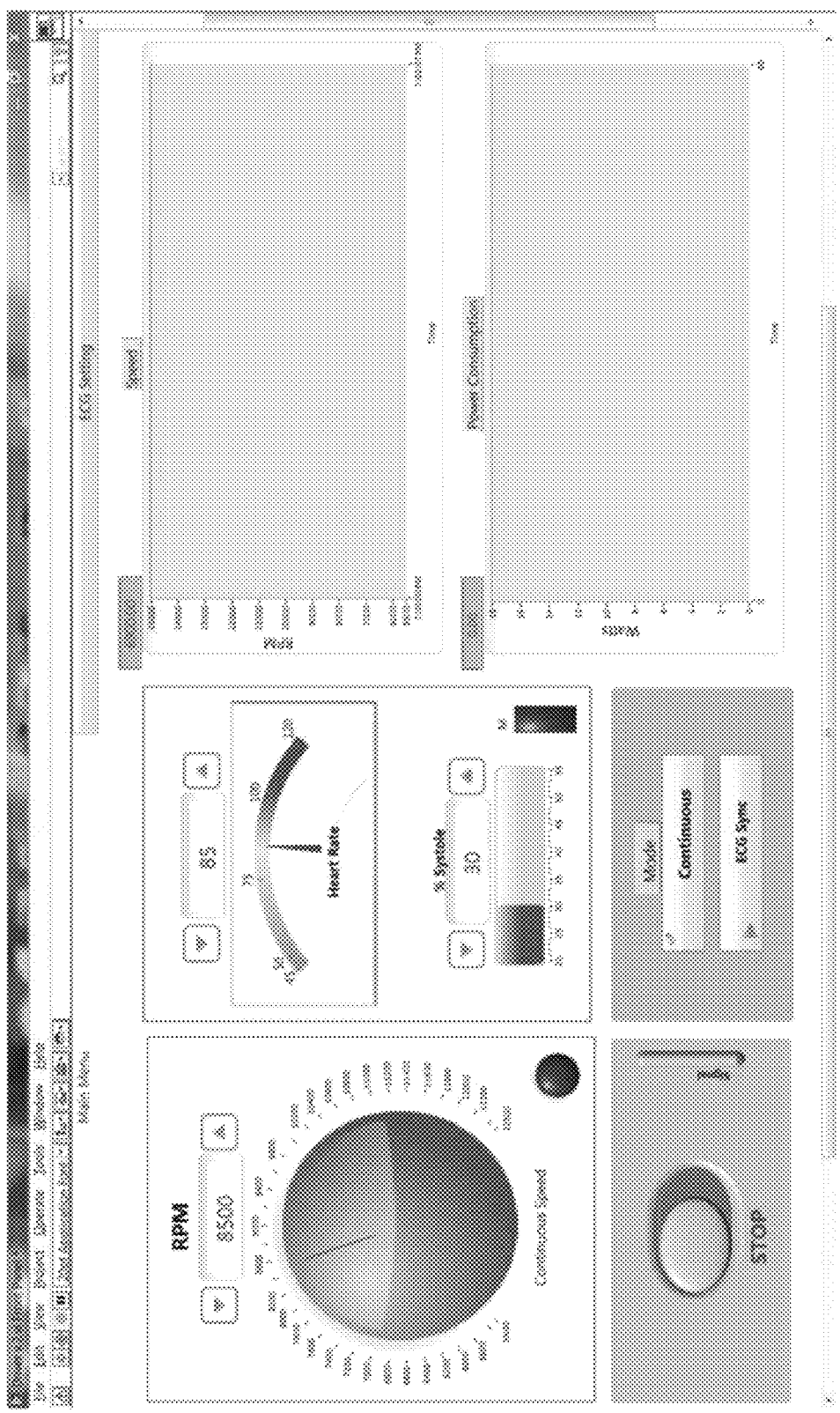
FIG. 3 is an image of an exemplary graphical user interface main menu of an exemplary system of the invention.
Figure 4:
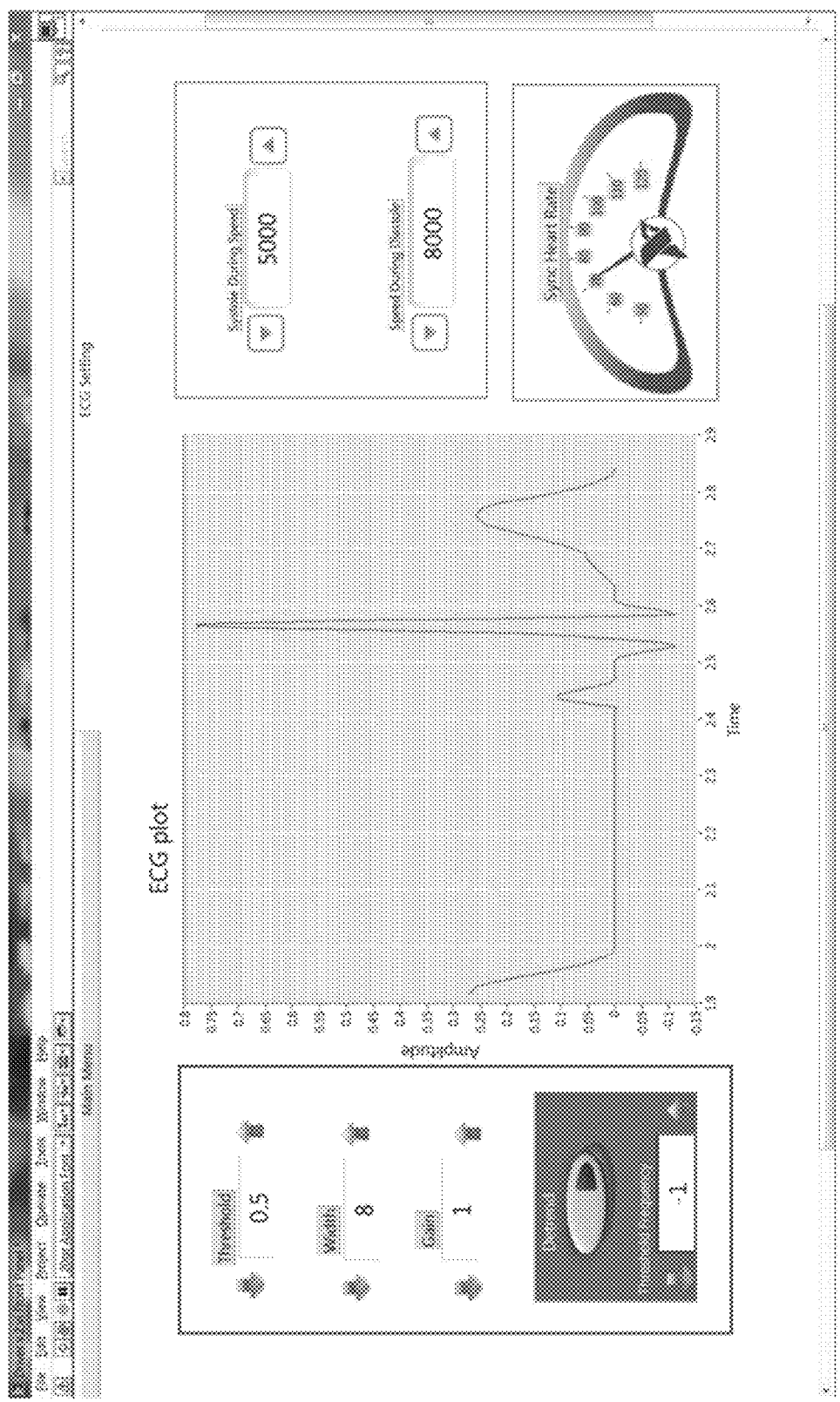
FIG. 4 is an image of an exemplary graphical user interface of EKG settings of an exemplary system of the invention.

The software may include a software framework or architecture that optimizes ease of use of at least one existing software platform, and that may also extend the capabilities of at least one existing software platform. The software provides applications accessible to one or more users (e.g. patient, clinician, etc.) to perform one or more functions. Such applications may be available at the same location as the user, or at a location remote from the user. Each application may provide a graphical user interface (GUI) for ease of interaction by the user with information resident in the system. Exemplary GUIs of the invention are provided in FIGS. 3 and 4, which depict the ability for a user to control the function or mode of the device, as well as the ability to display cardiac function. A GUI may be specific to a user, set of users, or type of user, or may be the same for all users or a selected subset of users. The system software may also provide a master GUI set that allows a user to select or interact with GUIs of one or more other applications, or that allows a user to simultaneously access a variety of information otherwise available through any portion of the system. Presentation of data through the software may be in any sort and number of selectable formats. For example, a multi-layer format may be used, wherein additional information is available by viewing successively lower layers of presented information. Such layers may be made available by the use of drop down menus, tabbed pseudo manila folder files, or other layering techniques understood by those skilled in the art.

The software may also include standard reporting mechanisms, such as generating a printable results report, or an electronic results report that can be transmitted to any communicatively connected computing device, such as a generated email message or file attachment. Likewise, particular results of the aforementioned system can trigger an alert signal, such as the generation of an alert email, text or phone call, to alert a patient, doctor, nurse, emergency medical technicians, or other health care provider of the particular results.

Figure 15:
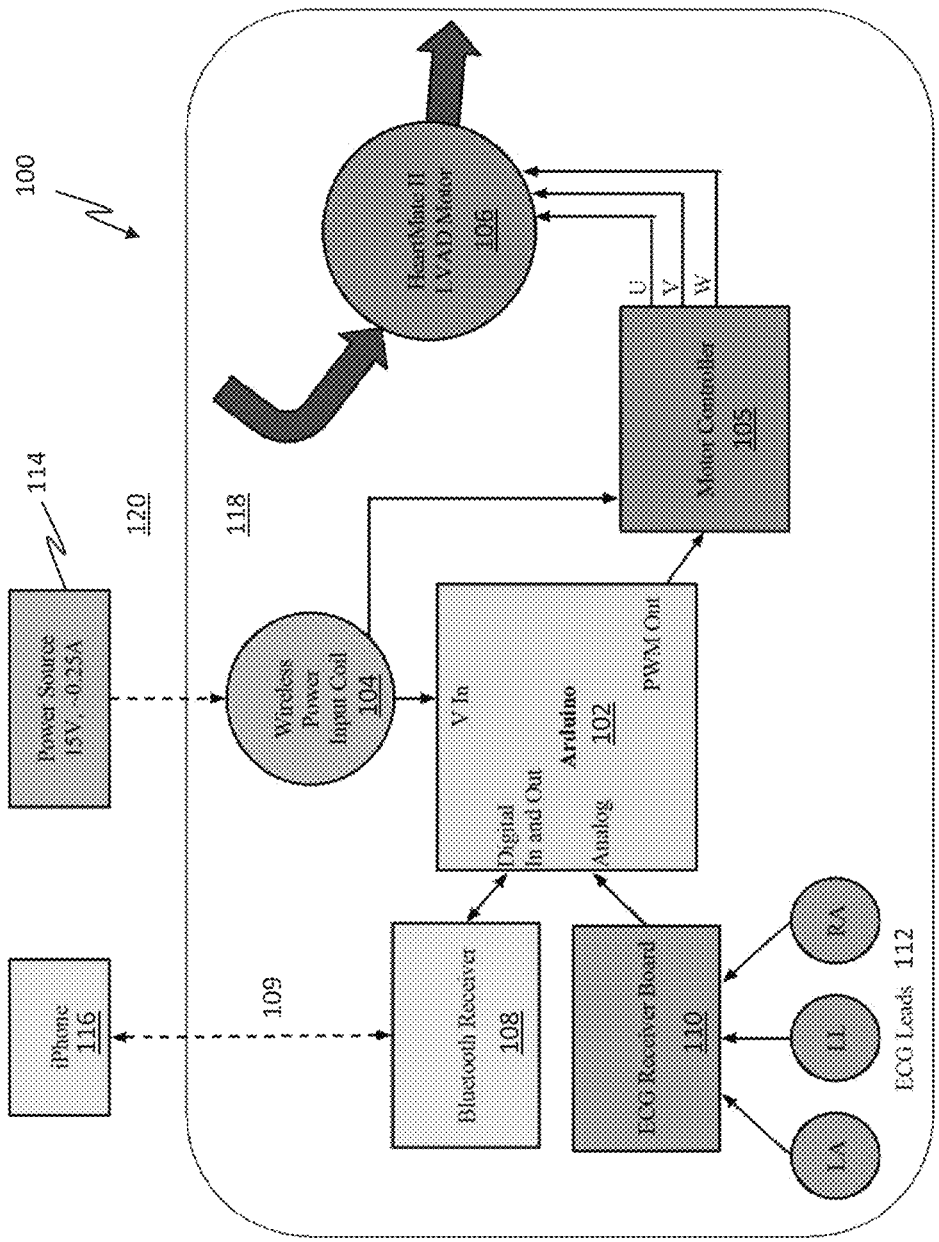
FIG. 15 is a diagram of a system for remotely monitoring the patient and an implanted LVAD, and for controlling the implanted LVAD remotely, according to one embodiment.
Figure 17:
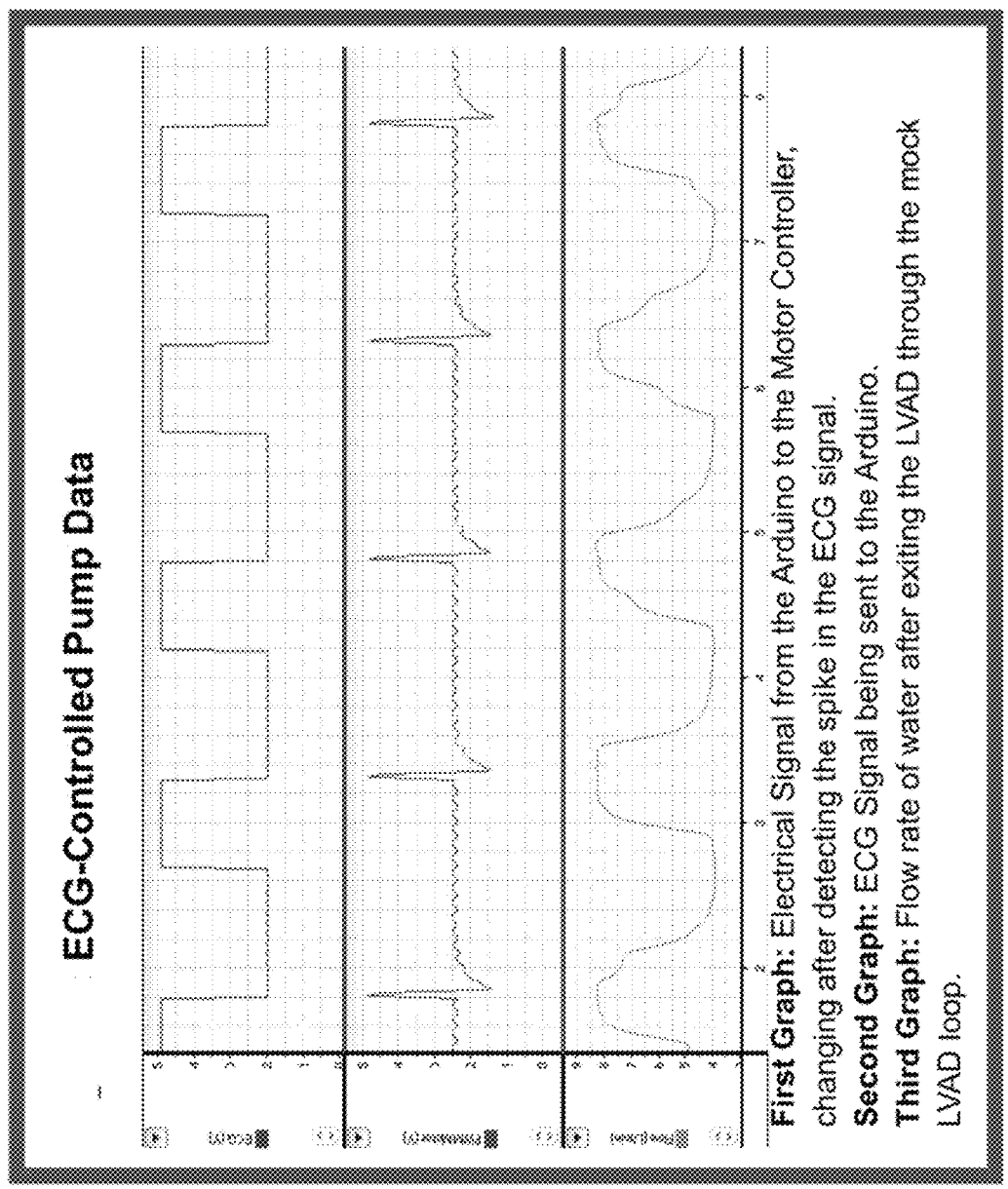
FIG. 17 is an example of waveform data that can be viewed on a GUI for display on a patient or physician remote or mobile device, according to one embodiment.

Wireless LVAD technology can eliminate the risk of driveline infection, which previously occurred in approximately 60% of patients. Systems and methods to monitor and control pump parameters can also be included. Patients and physicians must have access to information including pump speed to maintain control over the LVAD. In one embodiment, as shown in FIG. 15, a system 100 is centered around a processor 102, which runs regardless of whether or not a wireless connection 109 to a mobile device 116 is established. In one embodiment, the processor 102 is a microprocessor, such as the Arduino Uno, and Bluetooth 109 is utilized as the wireless communication protocol between a smart phone 116 and a Bluetooth receiver 108 electrically coupled to the Arduino 102. ECG leads 112 are connected to an ECG receiver board 110, which is electrically coupled to the processor 102. In one embodiment, if a connection error is detected, such as if the ECG leads 112 produce interference, the Arduino 102 will automatically revert from a pulsatile pump mode to a continuous flow mode. Alternatively, in certain embodiments, the processor 102 will automatically revert from a pulsatile pump mode to a continuous flow mode if a connection error such as a weak or dropped wireless connection with external devices is detected. Data transmission protocols and other protocols known in the art for detecting connection errors can be implemented for assessing the strength of the connection. A threshold can be set to trigger the error when the connection strength or accuracy level drops below the threshold. The processor 102 is connected to a wireless power input coil 104, implanted within the body 118, and is charged through energy transfer by an external power source 113 that remains outside 120 the body 118. The processor 102 sends output signals to a motor controller 105, which sends output signals to the LVAD motor 106 for controlling motor 106 functions such as speed and pulsing. In one embodiment, the motor controller 105 sends one signal to the LVAD motor 106 for controlling motor function. In one embodiment, the motor controller 105 sends multiple signals, such as U, V and W to the motor 106 for controlling motor function. In one embodiment, the modules of the system 100 within the body 118 are housed in a single housing, with ECG leads 112 extending away from that housing. In one embodiment, the electronic system 100 that interfaces the LVAD 106 with a smart phone or tablet such as the iPhone 116 includes the microprocessor 102 (such as the Arduino Uno), a motor driver 105 (such as the Koford S24V5A), a Bluetooth extension board 108 (such as the Adafruit nRF8001), and an ECG board 110 (such as the Olimex). The microprocessor 102 controls LVAD 106 functions such as pulsing, motor speed and mode (e.g. pulsing or continuous mode). The motor driver 105 provides a pulse width modulated (PWM) signal to control LVAD 106 speed. The Bluetooth board 108 communicates with an iPhone 116 and the ECG board 110 calculates an ECG wave from one or more leads (e.g. three leads) and sends data to the microprocessor 102. The microprocessor is coded to detect a fiducial point in the waveform, such as the R spike in an ECG wave, subsequently sending a pulsatile signal to the motor controller and calculating heart rate. An exemplary code for determining the R-spike is shown in FIG. 16. In one embodiment, a smart phone (i.e. iPhone) application was coded to receive and display data, such as patient heart rate, and control LVAD motor speed. A simulation of data that can be displayed on a mobile device is shown in FIG. 17. In one embodiment, the display includes one or more of a motor drive signal, an ECG signal, and a flow rate signal of fluid flowing through the LVAD. The system was tested in a bench-top mock circulation loop using blood analogue. Data shows ECG, the pump speed signal, and resulting flow rate (see data in FIG. 17). The delay between the electrical signal and the increase in flow ranged from 397 to 348 ms, varying with heart rate. The difference between maximum and minimum flow produced during pulsatile pump operation decreased as heart rate increased. The mobile application continuously received, analyzed, and controlled the wireless LVAD speed.

Advantageously, LVAD system according to the embodiments discussed herein successfully integrate communication with systems such as iOS hardware to allow for easy and secure viewing and storage of data. The processor (e.g. the Arduino) utilizes monitored data such as ECG data for intelligent pump control, such as pump speed control during systolic and diastolic phases. By interfacing the LVAD with sensors in the body, powering the LVAD with wireless energy, and communicating data to and from the LVAD using a wireless device, embodiments of LVAD systems disclosed herein have numerous advantages, including: no sepsis risk, lowered ventricular collapse risk, complete portability, compatibility with modern telemedicine systems, easily monitored and controlled, and easy interfacing with body sensors and other artificial body parts.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: A Physiological, Pulsatile Driver for Continuous Flow Left Ventricular Assist Device (LVAD): Innovation Using an Implantable Ultra-Compact Microcontroller with a Wireless Graphical User Interface Described herein is the demonstration of an ultra-compact implantable microcontroller (UMC-Physio) (FIG. 5A) capable of pulsed operation in a rotary pump with wireless communication to a graphical user interface outside the body.

Figures 5A, 5B:
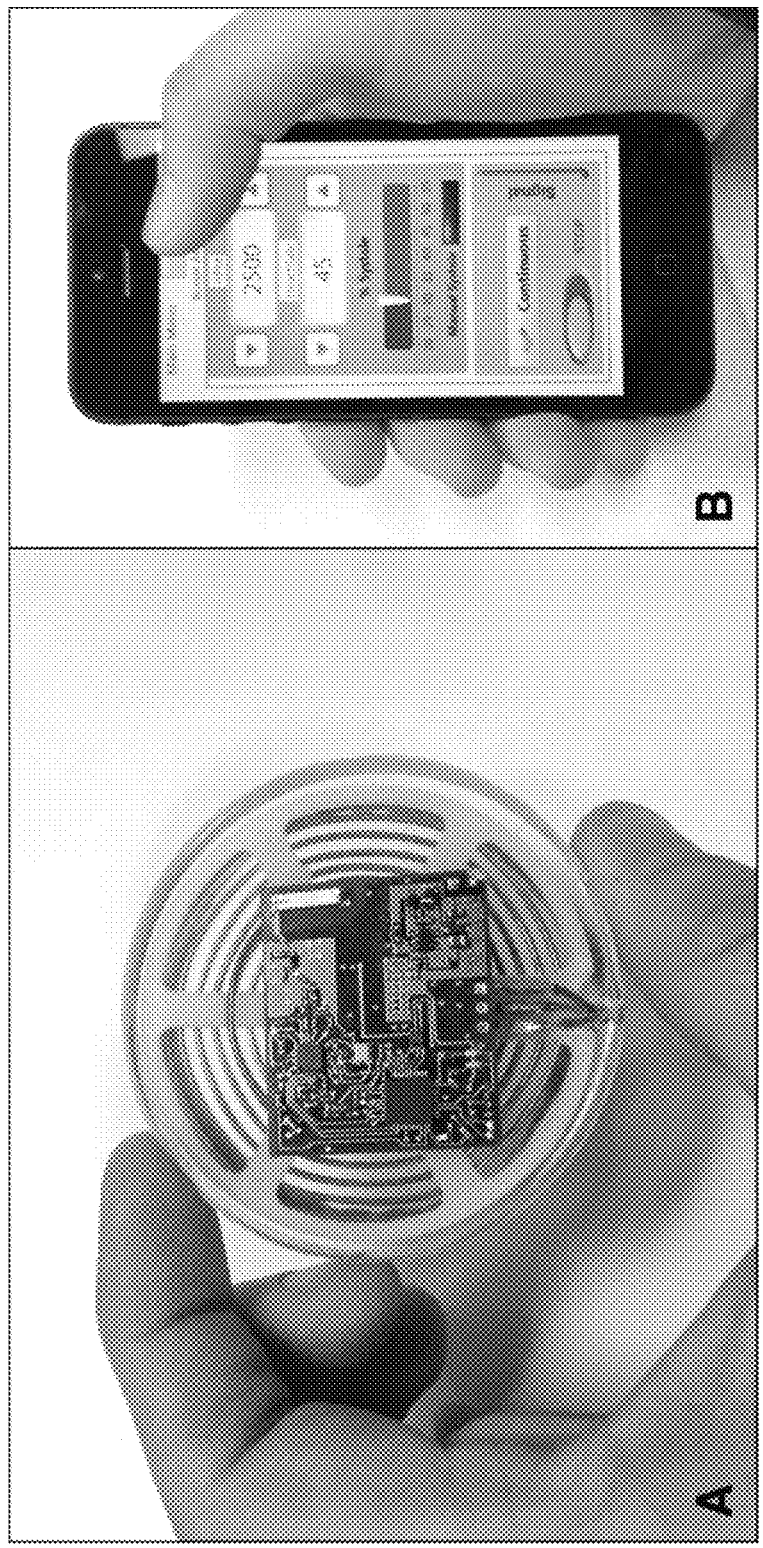
FIGS. 5A and 5B are a set of images depicting a controller (UMC-Physio) coupled with the FREE-D receiver coil to wirelessly obtain power and run an LVAD pump (FIG. 5A).

A three phase axial pump (HeartMate II) was used with an inline controller designed on an ultra-compact printed circuit board with embedded wireless algorithm to establish a communication network between the UMC-Physio and a graphical user interface to display the information and configuration settings on a computing device, such as a smartphone (FIG. 5B).

Signal processing and filtering methods were employed to analyze EKG signal and to adjust speed during systole and diastole for a co-pulsation, counter-pulsation or a fixed mode operation. Flow was estimated by recording the changes in power consumption and speed controlled by the UMC-Physio in a mock circulation loop (MCL). A suction event detection algorithm was incorporated in the system for additional safety. Finally, the UMC-Physio was tested and calibrated in combination with a HeartMate-II LVAD to ensure its accuracy.

Figure 6A:
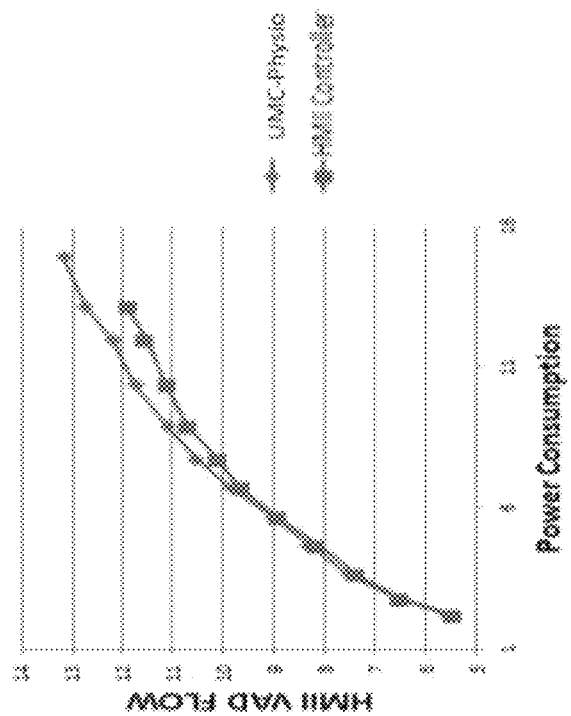
FIGS. 6A and 6B depict the functionality of the system.
Figure 6B:
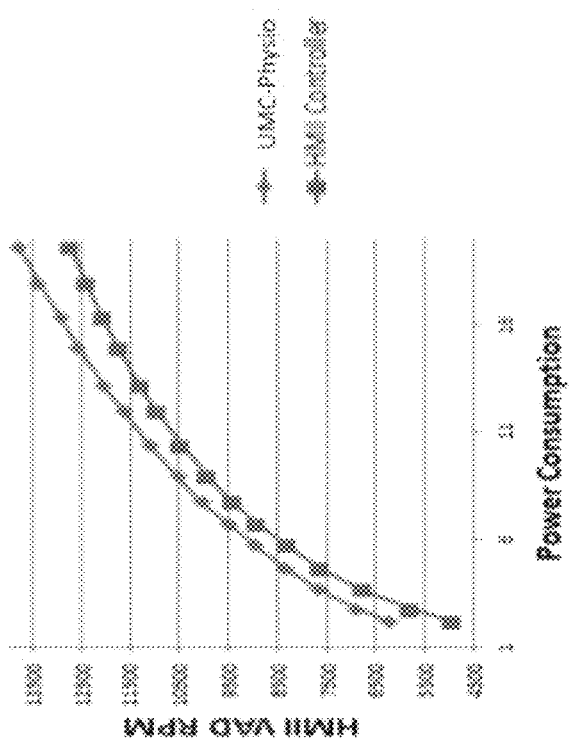

Test results prove the system to be remarkably safe, accurate and efficient. The UCMC-Physio operated continuously for two weeks duration with excellent communication. FIGS. 6A and 6B show that the UMC-Physio produces a same pump speed and flow rate at lower power consumption than the HeartMate II controller. When used with EKG gating the UMC-Physio allows different modes of operation with instantaneous flow and RPM changes resulting in a pulsatile flow with adjustable pulse pressure. The driver worked well with both axial and centrifugal pumps. The driver was capable of simulating physiological flow that worked well with a conventional continuous flow pump. Additional flexibility of wireless powering and communication with a user-friendly graphic display with a very small footprint makes this an ideal totally implantable LVAD system.

Example 2: Implantable Physiologic Controller for Left Ventricular Assist Devices with Telemetry Capability Rotary type left ventricular assist devices have mitigated the problem of durability associated with earlier pulsatile pumps and demonstrated improved survival. However, the compromise is the loss of pulsatility due to continuous flow and retained percutaneous driveline leading to increased mortality and morbidity. Lack of pulsatility is implicated in increased gastrointestinal bleeding, aortic incompetence, and diastolic hypertension. Presented herein is a novel, wirelessly powered, ultra-compact, implantable physiologic controller capable of running a left ventricular assist device in a pulsatile mode with wireless power delivery.

The schematic of the presently described system was laid out on a circuit board to wirelessly receive power and run a left ventricular assist device with required safety and backup measures. An antenna and wireless network for telemetry was embedded into the system. Multiple signal processing steps and controlling algorithm were incorporated. As described herein, the controller was tested in in vitro and in vivo experiments. The controller drove left ventricular assist devices continuously for 2 weeks in an in vitro setup and in vivo without any failure. The controller is more power efficient than the current Food and Drug Administration-approved left ventricular assist device controllers When used with electrocardiography synchronization, the controller allowed on-demand customization of operation with instantaneous flow and revolutions per minute changes, resulting in a pulsatile flow with adjustable pulse pressure. These test results prove the system to be remarkably safe, accurate, and efficient. The unique combination of wireless powering and small footprint makes this system an ideal totally implantable physiologic left ventricular assist device system.

In the current example, a UMC-Physio is again presented, which entirely untethers patients from the LVAD driveline, increases patients' quality of life, and significantly reduces complications associated with nonphysiologic continuous flow.

The materials and methods employed in these experiments are now described.

Left Ventricular Assist Device Motor

Current-generation LVADs are based on brushless direct current motors, also known as electronically commutated motors that are powered by a direct current electric source. An LVAD has 3 sets of coils positioned around its impeller. Once a coil is energized, it produces a magnetic field that causes the permanent magnet on the rotor to align with that magnetic field, which in turn rotates the impeller. However, the rotating action stops when the rotor is aligned with the magnetic field created by the energized coil. To keep the impeller in motion, the coils are energized in a particular sequence (120° out-of-phase from one another). The process of activating and deactivating the coils to keep the impeller spinning is termed "commutating."

Pump Speed

Because an LVAD does not have any sensor, the speed of the pump is measured from back electromotive force (EMF) generated by the motor's rotation. The amplitude of the back EMF is proportional to the angular velocity of the LVAD, but its shape will not change with speed and only depends on the pump characteristic. The present controller uses attenuation and filtering processing to sense this signal. The attenuation is required to bring the signal down to an allowable common mode range of the sensing circuit, and the low pass filtering is necessary for smoothing the high switching frequency noise.

When to Commutate and Power Efficiency

The challenge in controlling a brushless direct current motor is knowing when to commutate, because commutation must occur at precise points during rotation for the motor to have maximum torque and smooth operation. Because the implanted system must comply with the highest efficiency, a control algorithm was incorporated that spins the motor more efficiently to reduce the overall power consumption by calculating when to commutate on the basis of the back EMF of the motor. To further reduce the power, a sleep mode was introduced into the system that wakes the controller up at only certain point for a short amount of time (5 ms/s) to capture the sensor data and monitor the device operation.

Mode of Operation (Mimicking Physiologic Flow)

Figure 7A:
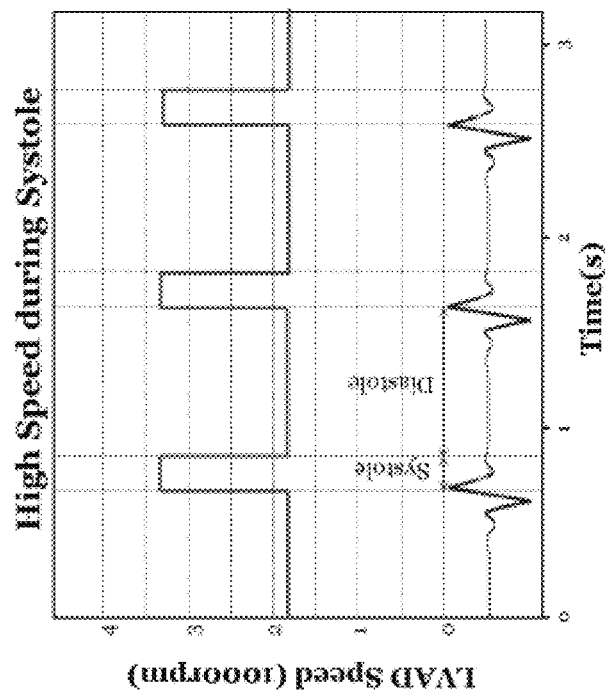
FIGS. 7A and 7B are graphs depicting the LVAD speed as controlled by the system of the invention in two different modes of use.
Figure 7B:
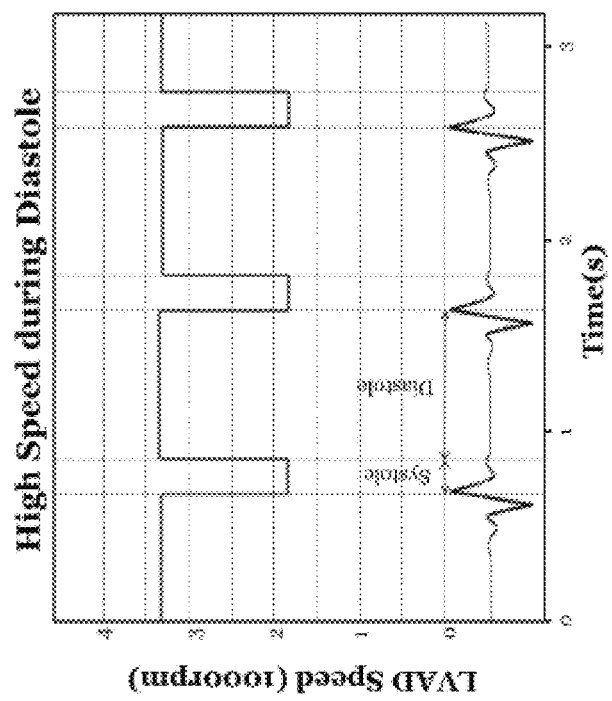

The purpose of an LVAD physiologic controller is to match the aortic pressure to a certain value derived from the patient activity. The UMC-Physio has 2 different modes of operation to mimic physiologic flow: continuous and pulsatile modes. In the continuous-flow mode, the user can set 1 speed. However, for the pulsatile mode, the user is required to define separate speeds during systole and diastole. Moreover, in case of a patient with potential myocardial recovery, the controller will have a higher speed during diastole and a lower speed during systole to decrease the preload of the heart (FIG. 7A). This allows the left ventricle to pump less blood during systole, which means less work for the left ventricle (Pirbodaghi et al., 2013, Eur J Cardiothorac Surg, 43: 383-8). In the event when a higher pulse pressure is necessary, such as patients with gastrointestinal bleeding, the system uses a higher speed during systole and a lower speed during diastole to create a larger pulse (FIG. 7B). The difference between systolic and diastolic pump speeds is called "ΔRPM."

Signal Processing

The pulsatile algorithm in the controller needs to swiftly modulate the pump speed to be able to gate it with an electrocardiography (ECG) signal for co-pulsation, counterpulsation, or fixed operation modes. Thus, the response time of the system is of a unique interest, because heart rates up to 120 beats/min with 30% systolic duration would produce a limit of a window of 0.15 second for the period of systole. Amplifiers and signal processing and filtering methods are used to further analyze an ECG signal.

Communication

Many medically implanted devices use wired or wireless methods to communicate with their external circuitry. Furthermore, an antenna, a transceiver unit (transmitter and receiver), and a wireless network algorithm are integrated into the controller to enable the UMC-Physio to establish a reliable telemetry communication with an extracorporeal platform, such as a smart phone, tablet, or personal computer. In wireless networking, the amplitude and width of the data pulses are kept constant in the system. The position of each pulse is varied by instantaneous sampled value of the modulating wave. This method is called "pulse position modulation." The controller puts out a stream of pulses called "sync pulses," which the external receiver recognizes with a circuitry called "phase locked loop." To create synchronization, an oscillator in the phase locked loop generates pulses at the same frequency as the controller.

Backup and Safety

Because the system is powered by using a FREE-D emitted electromagnetic fields, consideration was had that the noise potential might influence the proper function of the electronic implant. To significantly reduce the EMF susceptibility of the controller, multiple filtering mechanisms, ground isolation, and ground decoupling were combined in the design. Backup motor driver, overvoltage, and overcurrent protection circuits, thermal shutdown circuit, and independent pulse width modulation generator are among other safety issues that have been incorporated in the design. In addition, a suction event detection algorithm also was incorporated in the system for additional safety by detecting power consumption peaks that are abnormal.

Design and Development

The schematic of the system was laid out on a compact 4-layer printed circuit board using Altium Designer software (Altium, Australia) to run a rotary blood pump with required safety and backup measures. The control algorithms and graphical user interface were further developed in IAR System and LabVIEW software (both National Instruments, Austin, Tex.) respectively. The final system was coupled with an alternating current to direct current converter and a receiver coil to wirelessly receive power (FIG. 5A).

In Vitro Experiments

Figure 8:
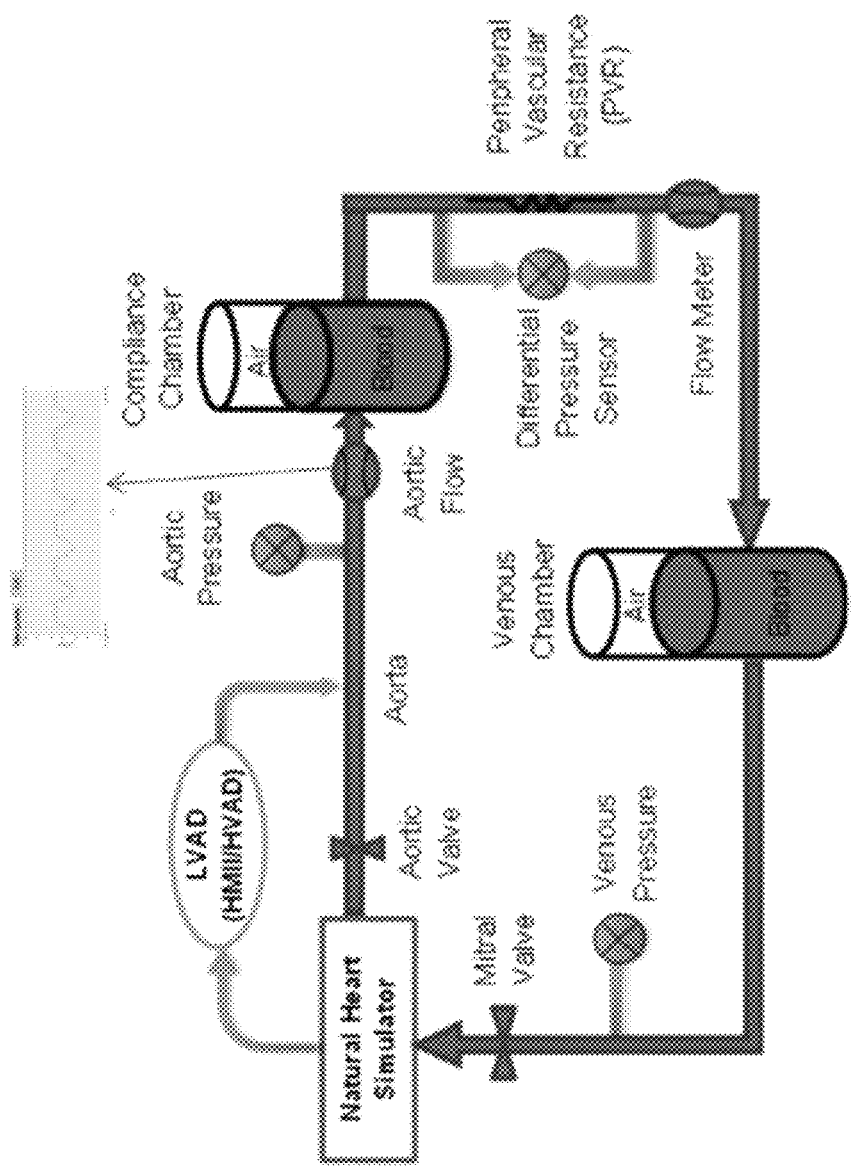
FIG. 8 is a schematic depicting an in vitro test setup where an LVAD pump is placed in an MCL. The pressure and flow are measured by the corresponding sensors. HMII, HeartMate II; HVAD, HeartWare Ventricular Assist Device; LVAD, left ventricular assist device.

The UMC-Physio initially was tested in a mock circulation loop (MCL) with the HeartMate II (Thoratec Co, Pleasanton, Calif.) and HeartWare Ventricular Assist Device (HeartWare Inc, Framingham, Mass.) pumps (FIG. 8). For the continuous mode, the UMC-Physio ran the HeartMate II axial pump for 2 weeks. The pump speed was gradually increased from 6000 up to 13,000 revolutions per minute (rpms) to ensure functionality. Next, the UMC-Physio drove the centrifugal pump for a 2-week period. The speed of the LVAD was changed from 1800 to 4000 rpms by 100 rpm steps.

For the pulsatile mode, both axial and centrifugal pumps were tested in the MCL. The fraction of systole was gradually increased from 20% to 80%, and the mean LVAD flow, produced by the controller, was measured at various heart rates. In the second test, systolic, diastolic, mean aortic, and pulse pressure were measured. Further, it was investigated how the UMC-Physio automatically increases the mean LVAD flow with increase in heart rates of 40 to 120 beats/min. These were then verified by changes in ΔRPMs. Moreover, the pump's outlet flow was estimated by recording the changes in power consumption and speed of the controlled LVAD in the MCL. The estimated flow was compared by the actual flow measured by the Transonic Flow Sensor (Transonic System Inc, Ithaca, N.Y.) to ensure its accuracy.

In Vivo Experiments

For the in vivo testing, the combination of the physiologic controller and HeartWare Ventricular Assist Device pumps was implanted in 2 large female pigs. In vivo experiments were performed to investigate the feasibility and implantability of the controller, to study its interference with biological tissue and temperature increase, to examine the effect of tissue impedance on telemetry communication, and to prove system capability of introducing pulsatile flow in the animals. The experiments were performed without any manipulation in the animal's vasomotor system (during the pulsatile mode, the preload, afterload, and contractility were not manipulated with inotropic infusions and were kept in steady state before initiating pulsatile mode).

The surgical approach briefly consisted of induction by intravenously administered anesthesia. The animals were then intubated and ventilated. The animals were maintained on isoflurane anesthesia throughout the surgery. External ECG was set up via needle electrodes in the extremities. A dwell-time silicone catheter was placed in the right internal carotid and external jugular vein for pressure monitoring. A 16 g catheter was placed in the left external jugular vein for fluid maintenance and monitoring of the central pressure in the heart. In addition to the central line, an intravenous catheter was placed in the cephalic or saphenous veins. Once the animals were instrumented, systolic and diastolic pressure, central venous pressure, heart rate, rectal temperature, oxygen saturation, and end-tidal carbon dioxide were monitored continuously and whole blood sample was collected for immediate hematocrit, coagulation profile, and blood gases for regular assessment.

The chest of the animal was opened via a left lateral thoracotomy at the fifth/sixth intercostal space, and the small portion of the fifth rib was removed at the costochondral junction. Surgery was performed without the use of cardiopulmonary bypass. The descending aorta was exposed, and the azygous vein was separated.

A dose of heparin was administered to obtain an activated clotting time greater than 400 seconds in preparation for anastomosis of the outflow graft to the descending thoracic aorta. The graft was placed transdiaphragmatically, positioned dorsally to prevent atelectasis of the lung, and anastomosed end-to-side to the aorta. Antiarrhythmics were administered in preparation for insertion of the inlet of the pump into the left ventricle of the heart. Teflon pledgeted sutures were placed radially around the left ventricular apex, and a 10- to 12-mm core of the apex was removed using a circular trocar. The HeartWare Ventricular Assist Device inlet cannula was placed in the ventricle. The inlet of the pump was secured by suturing of the cannula sewing-ring to the apical pledgets.

The animal experiment was designed to test for the following parameters: bio-interference, thermal changes, tissue impedance, telemetry communication, continuous mode operation, and pulsatile mode operation.

Statistical Analyses

The correlation among the variables (pump flow, heart rate, diastolic pressure, systolic pressure, and pulse pressure) was tested by Pearson correlation for all observations, in which a 2-tailed P value less than 0.05 shows the existence of statistically significant correlation between 2 variables. Furthermore, Pearson correlation measures the strength and direction of the linear relationship between the 2 variables. The correlation coefficient can range from −1 to +1, with −1 indicating a perfect negative correlation, +1 indicating a perfect positive correlation, and 0 indicating no correlation at all. In addition, linear, logarithmic, and cubic regressions were used where appropriate for examining relations between correlated variables.

In Vitro Results

The UMC-Physio tolerated dynamic power fluctuations introduced by wireless power delivery. During each 2-week in vitro testing with axial and centrifugal pumps, there was no telemetry disconnection, thermal shutdown event, sudden speed changes, power dropout, or pump failure. Moreover, the graphical user interface embedded in an iPhone (Microsoft Corp, Redmond, Wash.), iPad (Microsoft Corp), and laptop allowed for the wireless observation of the recorded data and modification of the LVAD configuration (FIG. 5B).

Response to Physiologic Demands

When used with ECG gating, the UMC-Physio allowed on-demand customization of operation with instantaneous flow and rpm changes, resulting in a pulsatile flow with adjustable pulse pressure. The controller responds to increases and decreases in heart rate and automatically adjusts pump flow and pulsatility accordingly.

Axial Left Ventricular Assist Device (HeartMate II)

Figure 9E:
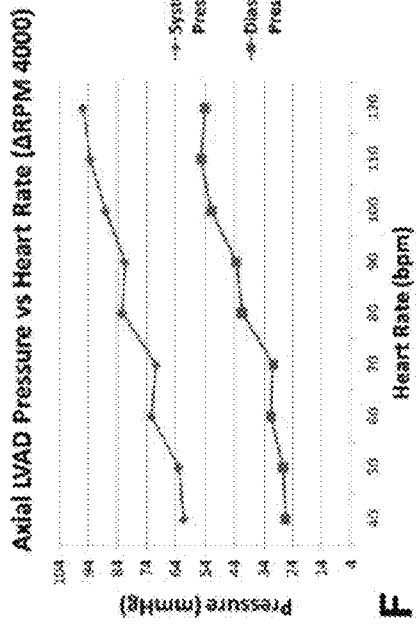
Figure 9F:
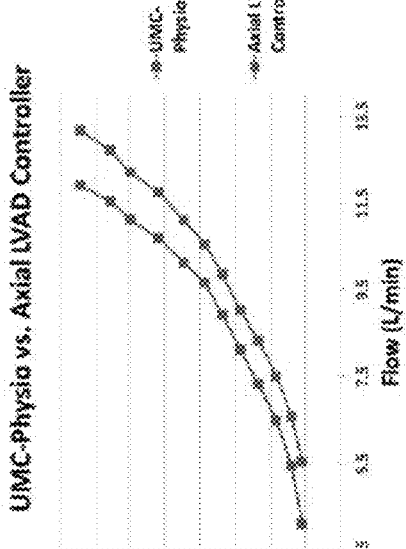

FIG. 9A demonstrates that the controller increases the mean flow of an axial pump by an average of 0.313 L/min per 10 beats/min change in heart rate. Likewise, 1000 ΔRPM increases the mean flow in this pump by an average of 0.24 L/min. The linear regression equation with $R^2$ of 0.981 is used; therefore, approximately 98% of the mean pump flow (L/min) is explained by heart rate and ΔRPM. This model is expressed as follows:

$$\text{Mean LVAD Flow (L/min)} = 0.031333 \cdot \text{Heart Rate (beats/min)} + 0.00024089 \cdot \Delta\text{RPM (rpms)} + 2.38056.$$

FIG. 9B shows that a 10% increase in fraction of systole leads to an increase of 0.29 L/min more mean flow in the system. The $R^2$ for this linear model is 0.975. The relationship (linear regression) is expressed as follows:

$$\text{Mean LVAD Flow (L/min)} = 0.02486 \cdot \text{Heart Rate (beats/min)} + 0.02934 \cdot \text{Fraction of Systole (\%)} + 1.8883.$$

FIGS. 9C-9F show that the UMC-Physio increases the systolic and diastolic pressures by increases in the heart rate. The linear regression is expressed as follows:

$$\text{Systolic Pressure (mm Hg)} = 0.44014 \cdot \text{Heart Rate (beats/min)} + 0.01041 \cdot \Delta\text{RPM (rpms)} + 2.02963$$
$$\text{and Diastolic Pressure (mm Hg)} = 0.41806 \cdot \text{Heart Rate (beats/min)} + 0.00042593 \cdot \Delta\text{RPM (rpms)} + 4.85185.$$

Figure 9G:
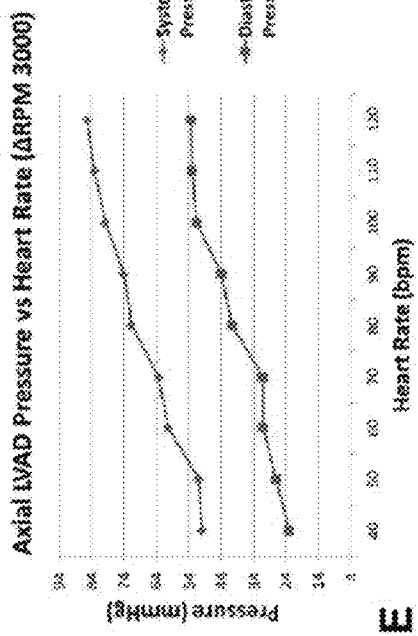
Figure 9H:
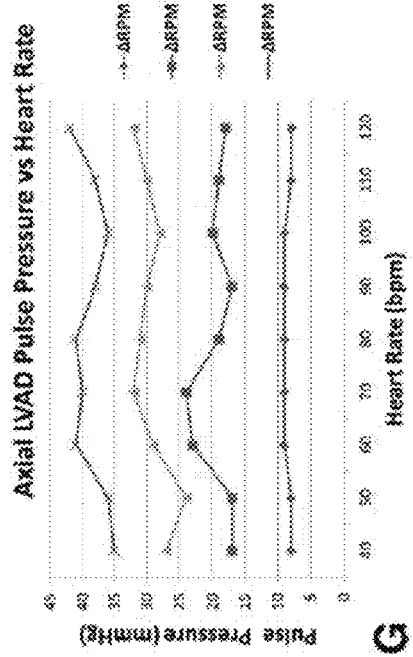

FIG. 9G shows that increase in ΔRPM creates more pulse pressure. FIG. 9H proves that the controller consumes less power compared with the HeartMate II controller to achieve the flow and speeds for the HeartMate II pump, being more efficient by a mean of 17.54%. The relation between efficiency and flow (independent variable) is estimated by curve approximation. As a result, the cubic model has been used because of its highest $R^2$ (0.999). The efficiency is estimated by the following:

$$\text{Efficiency (\%)} = 0.08309 \cdot \text{Flow}^3 + 1.897 \cdot \text{Flow}^2 + 13.907 \cdot \text{Flow (L/min)} \cdot 15.6778.$$

Centrifugal Left Ventricular Assist Device (HeartWare Inc)

Figure 10B:
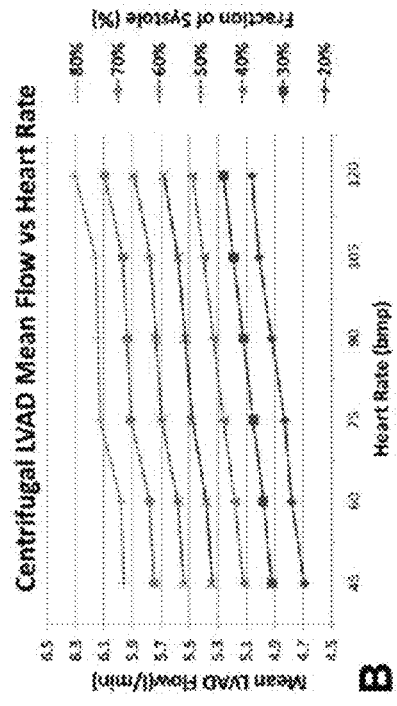
FIGS. 10A through 10H depict the results of in vitro testing with the HeartWare Ventricular Assist Device (HeartWare Inc, Framingham, Mass.) pump. The results are related to the MCL.
Figure 10D:
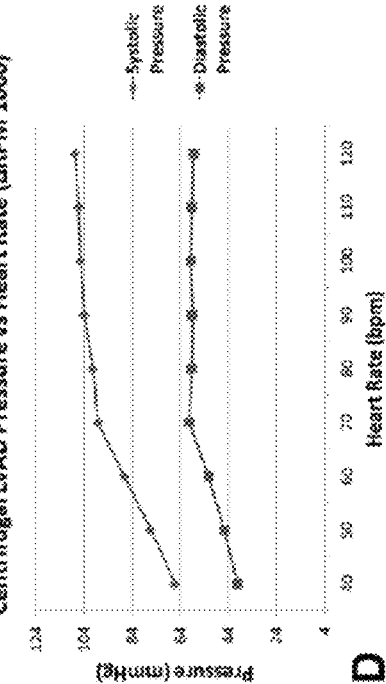
Figure 10A:
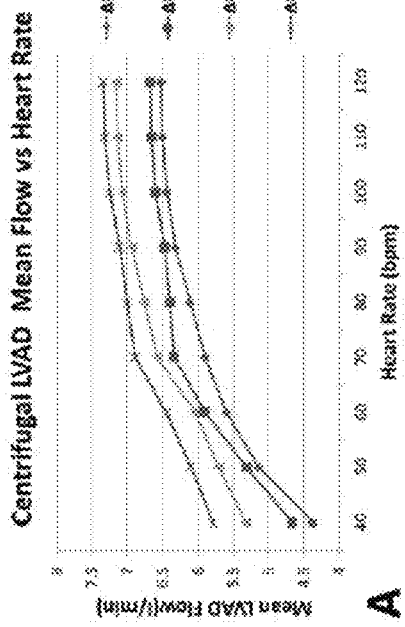
Figure 10C:
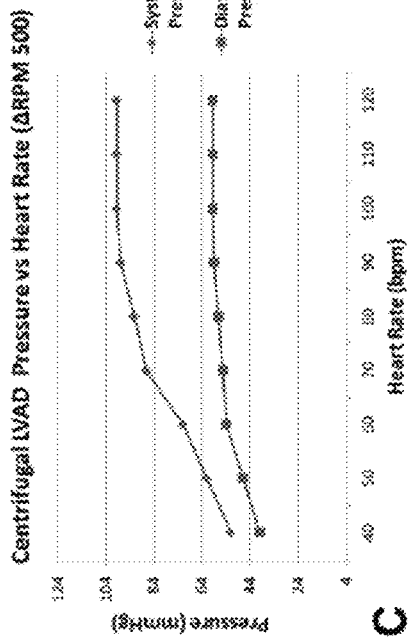
Figure 10F:
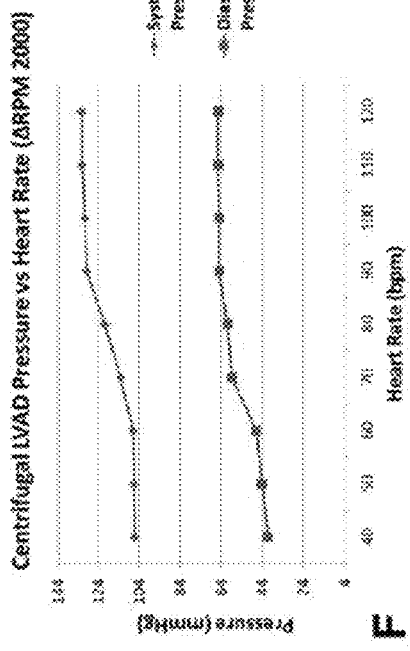

FIG. 10A reveals that the controller can increase the mean flow of a centrifugal pump by 0.22 L/min when the heart rate increases by 10 beats/min. Likewise, 500 ΔRPM increases the mean flow in this pump by an average of 0.319 L/min. The linear regression was used because of an $R^2$ value of 0.885. Thus, approximately 88% of the data in the LVAD mean flow are explained by heart rate and ΔRPM. The regression model for this graph is as follows:

$$\text{Mean LVAD Flow (L/min)} = 0.0226 \cdot \text{Heart Rate (beats/min)} + 0.000638222 \cdot \Delta\text{RPM (rpms)} + 3.7245.$$

FIG. 10B confirms that an increase in fraction of systole increases the mean by 0.2 L/min. The $R^2$ for this linear regression is 0.998; thus, approximately 99.8% of the data in LVAD mean flow are explained by heart rate and fraction of systole. The regression equation seems to be useful for making predictions because the value of $R^2$ is close to 1. This formula explains this linear regression:

$$\text{Mean LVAD Flow (L/min)} = 0.0046 \cdot \text{Heart Rate (beats/min)} + 0.0205 \cdot \text{Fraction of Systole (\%)} + 4.09312.$$

FIGS. 10C-10F demonstrates that the heart rates up to 80 beats/min that will increase the systolic and diastolic pressures produced by the controller and the LVAD. The systolic and diastolic pressures can be estimated by the following formulas:

Systolic Pressure (mm Hg)=0.50067·Heart Rate (beats/min)+0.02364·ΔRPM (rpms)+31.98556 and Diastolic Pressure (mm Hg)=0.26817·Heart Rate (beats/min)+0.00188·ΔRPM (rpms)+32.08556.

Figure 10H:
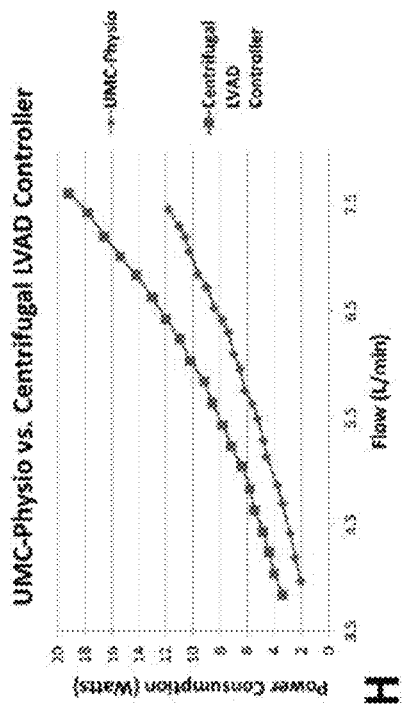
Figure 10E:
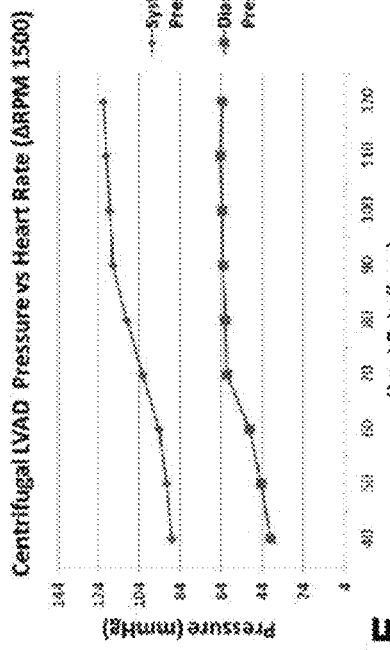
Figure 10G:
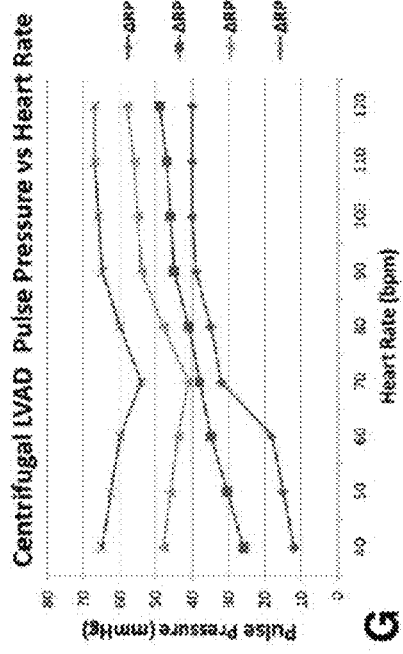

FIG. 10G, shows that pulse pressure can be easily controlled by the system. The linear regression is as follows:

Pulse Pressure (mm Hg)=0.2325·Heart Rate (beats/min)+0.02176·ΔRPM (rpms)−0.1.

FIG. 10H shows that the controller is more efficient that the HeartWare Ventricular Assist Device controller. The relation between efficiency and flow (independent variable) is estimated by cubic estimation because it has the highest $R^2$ compared with other models. The descriptive statistics indicate that our controller is more efficient by mean of 35.49%. Efficiency is modeled as follows:

Efficiency (%)=2.648·Flow$^2$−32.630·Flow (L/min)+132.964 (these results are based on the specific MCL that were used and can vary in a biological system).

In Vivo

Figure 11:
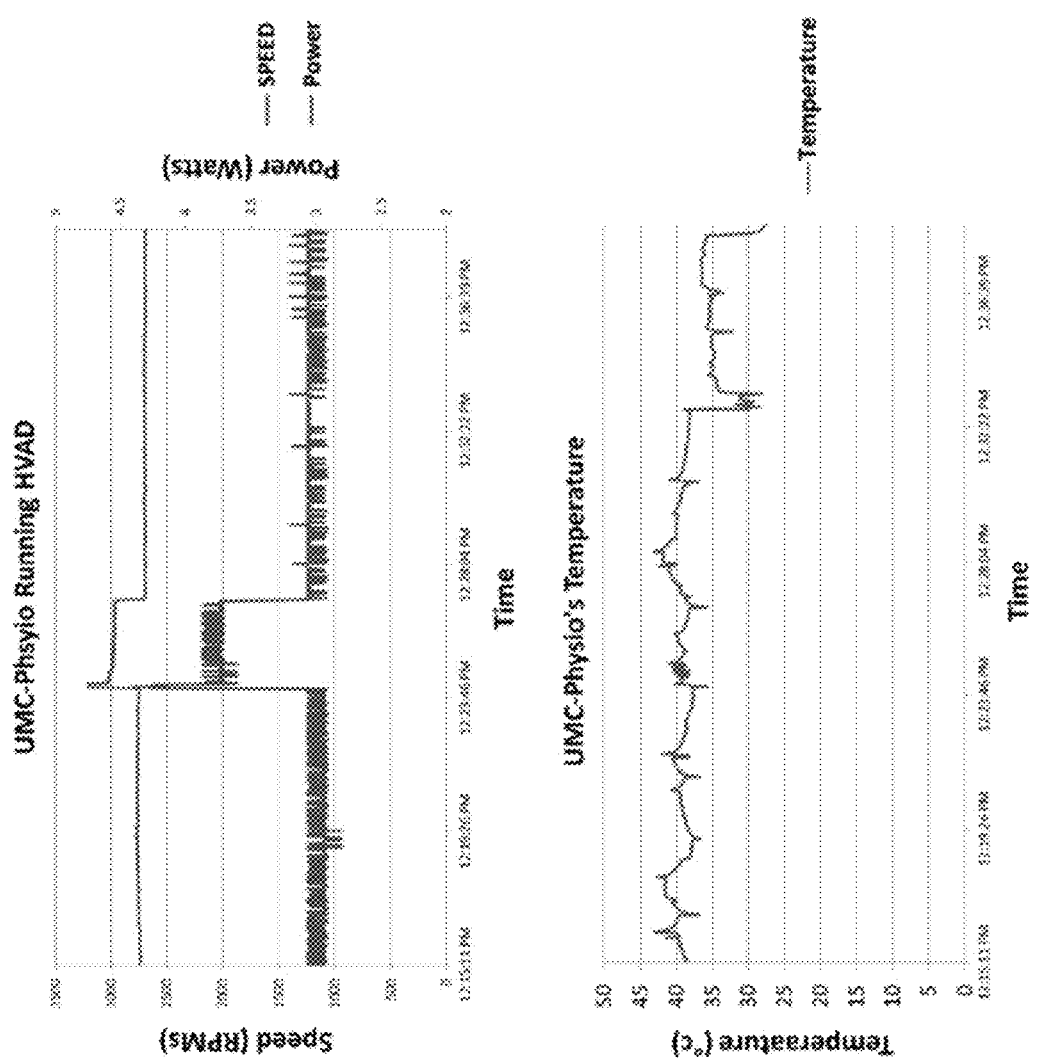
FIG. 11 depicts the results of experiments and depicts a representative demonstration of the power consumption and speed (top) of a HeartWare Ventricular Assist Device pump in one of the in vivo experiments. The consistent and smooth pump speed indicates how the controller adapts to the sudden changes of wireless power delivery. In addition, it displays the EMF noise-free telemetry data. The temperature of the implanted unit also is graphed (bottom) to illustrate there was no temperature increase in the unit that might affect the surrounding tissues. HVAD, HeartWare Ventricular Assist Device; RPM, revolutions per minute; UMC-Physio, ultra-compact implantable physiologic controller.

The controller successfully ran an untethered HeartWare Ventricular Assist Device pump for 3 hours in each animal with continuous and pulsatile modes (cumulatively 6 hours of experimental data). First, the ability of the controller to run the pump in the continuous mode was tested to assess power consumption in comparison with HeartWare Ventricular Assist Device controller. Then efficiency was tested as a baseline measure of overall controller performance. These studies showed that there was no biological tissue interference, temperature increase, or network mismatching in the system. The tissue impedance decreased communication distances. FIG. 11 also shows that the controller automatically adapts to the dynamic changes in the wireless power to create a steady pump speed.

The human heart and circulation have developed over millennia—starting from the primitive coelom that was a passive receptacle for gas exchange, feeding, and sexual reproduction lined by endoderm to subsequent lining of the coelomic cavity by mesodermal contractile cells, which became a "gastrovascular organ." Further differentiation into a peristaltic heart in Chordata and vertebrates leads to the sophisticated differentiation from a primitive tubular hearts into a looped, unidirectional circulation with a highly specialized conductive and pacemaker cells. The subsequent parallel pulmonary circulation was a further evolutionary step. The evidence to suggest the primordial gastrovascular structure to today's highly specialized cardiac structure is demonstrable by the common nerve supply to heart and gut by the central nervous system and the pulsatility that has been the hallmark of mammalian circulation for millennia (Bishopric, 2005, Ann NY Acad Sci, 1047: 13-29).

Rotary pumps use controllers that run an LVAD pump at a constant speed (Akimoto et al., 1999, Artif Organs, 23: 797-801). However, the continuous flow is mostly acceptable for short-term use of an LVAD (eg, bridge to transplant), but as we witness more widespread use and long-term support such as destination therapy, several unintended effects of continuous flow are becoming apparent (Demirozu et al., 2011, J Heart Lung Transplant, 30: 849-53; Crow et al., 2009, J Thorac Cardiovasc Surg, 137: 208-15; Amir et al., 2006, J Heart Lung Transplant, 25: 391-4; Westaby et al., 2007, J Thorac Cardiovasc Surg., 133: 575-6; Pirbodaghi et al., 2013, Heart Fail Rev; Cowger et al., 2010, Circ Heart Fail, 3: 668-74; Akimoto et al., 1999; Artif Organs, 23: 797-801). After all, the continuous flow associated with current LVAD devices was a result of replacing earlier pulsatile devices with a more durable pumping system at the cost of pulsed operation. The system of the present invention allows leveraging both the durability of rotary pumps and restoring the pulsed operation simultaneously.

Several researchers have tried to mimic nature by designing physiologic LVAD controllers by using proportional-integral (Parnis et al., 1997, ASAIO J., 43: M576-80; Waters et al., 1999, Artif Organs, 23: 480-6) and fuzzy logic (Choi et al., 2001, IEEE Trans, 9: 473-82; Boston et al., 2000, Proc 2000, 5: 3473-7) control algorithms to automatically modulate the constant speed of the pump. However, the present system combines adaptive optimal proportional feedback control algorithm, ECG gating, and head pressure and flow estimation to perform its physiologic modulation during systole and diastole. Previous studies (Yoshizawa et al., 20002, ASAIO J., 48: 443-8; Ayre et al., 2000, Artif Organs, 24: 585-8) produced acceptable results for the estimation of the pulsatile flow and head pressure, but they did not investigate the stability of the transient response of the pump flow. The transient response has been demonstrated (Tsukiya et al., 1997, Yoshizawa et al., 2002, ASAIO J., 48: 443-8; Karantonis et al., 2007, Conf Proc IEEE Eng Med Biol Soc, 2007: 1018-21). Moreover, the head pressure estimation observed in other studies (Giridharan and Skliar, 2006, Artif Organs, 30: 301-7) suffers from a time delay because of the use of excessive filtering. The present system uses a simple low-pass filter to estimate the transient and steady-state head pressure and flow. This method produces an instant result with no delay. Although the real-time estimation process requires extra computation, it is a simple way to substitute sensor implementation. All of the flow and head pressure estimations were performed in the MCL.

Prior attempts include magnets, capacitive communication, Bluetooth, WiFi, ultrasound, and other radio frequencies to wirelessly communicate with an implantable medical device. The capacitive intra-body communication requires electrodes to be placed on or near the skin. Of these, ultrasound and magnets have low transmission efficiency and range through the biological tissue and are challenging to miniaturize. Radiofrequencies, such as a medical implant communication service band or Wireless Medical Telemetry Service, require bulky antennas that restrict how small the controller can be. In the present system, industrial, scientific, and medical radio bands of 2.4 GHz with a highly automated communication was used that has a short wavelength and therefore a small size.

Data modulation has been accomplished by amplitude shift key, phase shift keying, continuous phase modulation, and other methods to translate data. The pulse position modulation method has the advantage of pulses with constant amplitude and width, but the disadvantage of requiring synchronization between transmitter and receiver. The obtained telemetric data during the experiments were noise-free from sources such as the EMF and pulse width modulation switching. The graphical user interface enables a physician to monitor and control the patient's LVAD even when not in wireless range of the implanted device by using the Internet to access the patient's external receiver that in turn relays the information to and from the implanted controller. The corresponding data can be placed in the database for future review and analysis.

The UMC-Physio rapidly synchronizes the pump to the heart rate to mimic physiologic flow to adapt to the patient's everyday physiologic demands. The controller can produce the same pump speed and flow rate at a lower power than the HeartWare Ventricular Assist Device and HeartMate II controllers, making it more efficient. The power consumption of the controller is extremely low because of the accurate commutation and sleep mode. The UMC-Physio enables an LVAD to be controlled digitally, bringing precise control, higher efficiency, and faster response time for this type of pump. The UMC-Physio can control both axial and centrifugal blood pumps.

The novel combination of wireless powering, a user-friendly interface, and a small footprint makes this an ideal totally implantable LVAD system. The data presented herein demonstrate the feasibility of a controller that can create versatile physiologic flow with a conventional continuous-flow pump.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A system for remote communication with an implantable ventricular assist device comprising:
    the implantable ventricular assist device configured to authenticate a communication session between the implantable ventricular assist device and a mobile device using a first key-id stored on the implantable ventricular assist device; and
    a software platform configured to verify a second key-id to authenticate a communication session between the mobile device and the software platform, the software platform further configured to verify a patient specific key received from a remote device to authenticate a communication session between the software platform and a remote device;
    wherein the software platform is configured to establish a communication session to send values from the remote device to the implantable ventricular assist device based on verifying all of the first key-id, the second key-id and the patient specific key.

2. The system of claim 1, wherein the patient specific key is based on the first key-id.

3. The system of claim 1, wherein the software platform is configured to generate the second key-id after detecting an initialization of a connection between the mobile device and the software platform.

4. The system of claim 1, wherein the software platform is a server.

5. The system of claim 1, wherein the remote device is a user computer.

6. The system of claim 1, wherein the remote device is configured to accept input of the values through a web-based portal.

7. The system of claim 6, wherein the values include at least one of systole power and diastole power.

8. The system of claim 6, wherein the values include all of systole power, diastole power and the patient specific key.

9. The system of claim 1, wherein the implantable ventricular assist device is configured to send feedback to the remote device after verifying all of the first key-id, the second key-id and the patient specific key.

10. The system of claim 9, wherein the feedback includes at least one of a heart rate and a pump speed.

11. A method for remote communication with an implantable ventricular assist device comprising:
    verifying a first key-id stored on the implantable ventricular assist device to authenticate a communication session between the implantable ventricular assist device and a mobile device;
    verifying a second key-id to authenticate a communication session between the mobile device and a software platform; and
    verifying a patient specific key to authenticate a communication session between the software platform and a remote device;
    wherein a communication session to send values from the remote device to the implantable ventricular assist device is authenticated based on verifying all of the first key-id, the second key-id and the patient specific key.

12. The method of claim 11, wherein the patient specific key is based on the first key-id.

13. The method of claim 11, wherein the second key-id is generated at initialization of connection between the mobile device and the software platform.

14. The method of claim 11, wherein the software platform is a server.

15. The method of claim 11, wherein the remote device is a user computer.

16. The method of claim 11 further comprising:
    accepting input of the values through a web-based portal.

17. The method of claim 16, wherein the values include at least one of systole power and diastole power.

18. The method of claim 17, wherein the values include all of systole power, diastole power and the patient specific key.

19. The method of claim 11 further comprising:
    sending feedback from the implantable ventricular assist device to the remote device after verifying all of the first key-id, the second key-id and the patient specific key.

20. The method of claim 19, wherein the feedback includes at least one of a heart rate and a pump speed.

* * * * *